(12) United States Patent
Allander et al.

(10) Patent No.: US 8,110,350 B2
(45) Date of Patent: Feb. 7, 2012

(54) **HUMAN *BOCAVIRUS* AND METHODS OF DIAGNOSIS AND TREATMENT**

(75) Inventors: Tobias Allander, Stockholm (SE); Bjorn Andersson, Stockholm (SE)

(73) Assignee: Karolinska Institutet Innovations AB, Stockholm (SE)

( * ) Notice: Subject to any disclaimer, the term of this patent is extended or adjusted under 35 U.S.C. 154(b) by 0 days.

(21) Appl. No.: 12/094,135

(22) PCT Filed: Aug. 16, 2006

(86) PCT No.: PCT/EP2006/008074
§ 371 (c)(1),
(2), (4) Date: May 16, 2008

(87) PCT Pub. No.: WO2007/057062
PCT Pub. Date: May 24, 2007

(65) Prior Publication Data
US 2008/0292654 A1 Nov. 27, 2008

Related U.S. Application Data

(60) Provisional application No. 60/737,576, filed on Nov. 17, 2005.

(51) Int. Cl.
*C12Q 1/70* (2006.01)

(52) U.S. Cl. .............................. 435/5; 435/7.1; 536/23.1

(58) Field of Classification Search ........................ None
See application file for complete search history.

(56) References Cited

U.S. PATENT DOCUMENTS 7,045,316 B2 * 5/2006 Nezu et al. .................... 435/69.1
2001/0053519 A1 * 12/2001 Fodor et al. ........................ 435/6

FOREIGN PATENT DOCUMENTS

WO 88/02026 3/1988
WO 2004/056390 7/2004

OTHER PUBLICATIONS

Allander et al., "Cloning of a human *parvovirus* by molecular screening of respiratory tract samples," Proceedings of the National Academy of Science, USA, vol. 102 No. 36, pp. 12891-12896 (Sep. 2005).*
GenBank DQ000495, "Human *bocavirus* isolate st1, complete genome," first available Aug. 2005.*
Chen et al., "Complete nucleotide sequence and genome organization of bovine *parvovirus*," Journal of Virology, vol. 60 No. 3, pp. 1085-1097 (Dec. 1986).*
GenPept NP_041402, "hypothetical protein BParVgp1 [*Bovine parvovirus*]," Apr. 2000.*
Allander, T., et al., "A virus discovery method incorporating DNase treatment and its application to the identification of two bovine *parvovirus* species," PNAS, 98(20):11609-11614, (Sep. 25, 2001).
Allander, T., et al., "Cloning of a human *parvovirus* by molecular screening of respiratory tract samples," PNAS, 102(36):12891-12896, (Sep. 6, 2005).
XP002405488: Database EMBL, Sloots, T.P., et al., "Human bocavirus strain QPID04-0007 NS1 gene, partial cds." Database accession No. DQ200648, (Created Oct. 6, 2005, updated Jan. 4, 2006).
XP002405489: Database EMBL, Bastien, N., et al., "Human bocavirus isolate CAN1545-04 nonstructural protein 1 (NP-1) gene, partial cds." Database accession No. DQ267770, (Created Nov. 15, 2005, updated May 28, 2006).
XP002405490: Database EMBL, Schwartz, D., et al., "Minute virus of canines non structural protein 1, NP1, virus protein 1, and virus protein 2 genes, complete cds." Database accession No. AF495467, (Created Apr. 21, 2002, updated Apr. 15, 2005).
Jones, M.S., et al., "New DNA viruses identified in patients with acute viral infection syndrome," J. Virol., 79 (13):8230-8236, (Jul. 2005).
Kantola, K., et al., "Recombinant expression of human bocavirus capsid proteins," J. Clin. Virol., 36 (Supp.2): S47-48 (2006). [Abstract].

* cited by examiner

*Primary Examiner* — Agnieszka Boesen
(74) *Attorney, Agent, or Firm* — Dann, Dorfman, Herrell & Skillman; Kathleen D. Rigaut

(57) ABSTRACT

Human parvovirus, genus Bocavirus, associated with respiratory tract infections in children. Nucleic acid and polypeptide sequences of the virus. Methods and products for diagnosing presence of bocavirus in a sample using nucleic acid probes or primers, or specific binding members such as antibodies. Methods and products for diagnosing past or present infection of bocavirus in an individual e.g. by serology testing. Viral nucleic acid, polypeptide and/or viral particles for generating immune response in an individual, including vaccine compositions.

6 Claims, 1 Drawing Sheet

SEQUENCE LISTING

<160> NUMBER OF SEQ ID NOS: 10

<210> SEQ ID NO 1
<211> LENGTH: 5217
<212> TYPE: DNA
<213> ORGANISM: Human bocavirus
<220> FEATURE:
<223> OTHER INFORMATION: Human bocavirus ST1 genomic DNA

<400> SEQUENCE: 1

```
caaggaggag tggttatatg atgtaatcca taaccactcc caggaaatga cgtatgatag    60
ccaatcagaa ttgagtattg aacctatata agctgctgca cttcctgatt caatcagact   120
gcatccggtc tccggcgagt gaacatctct ggaaaaagct ccacgcttgt ggtgagtcta   180
ctatggcttt caatcctcct gtgattagag ctttttctca acctgctttt acttatgtct   240
tcaaatttcc atatccacaa tggaaagaaa agaatggctg cttcatgca cttttagctc   300 atggaactga acaatctatg atacaattaa gaaactgcgc tcctcatccg gatgaagaca   360
taatccgtga tgacttgctt atttctttag aagatcgcca ttttgggct gttctctgca   420 aggctgttta catggcaaca actactctca tgtcacacaa acaaaggaat atgtttcctc   480
```

-continued

```
gttgtgacat catagttcag tctgagctag gagagaaaaa cttacactgc catattatag    540
ttgggggaga aggactaagc aagaggaatg ctaaatcatc ctgtgctcag ttctatggtt    600
taatactagc tgaaataatt caacgctgca aatctcttct ggctacacgt ccttttgaac    660
ctgaagaggc tgacatattt cacactttaa aaaaggctga gcgagaggca tggggtggag    720
ttactggcgg caacatgcaa atccttcaat atagagatcg cagaggagac cttcatgcac    780
aaacagtgga tcctcttcgc ttcttcaaaa actacctttt acctaaaaat agatgtattt    840
catcttacag caaacctgat gtttgtactt ctcctgacaa ctggttcatt ttagctgaaa    900
aaacttactc tcacactctt attaacgggc tgccgcttcc agaacattac agaaaaaact    960
accacgcaac cctagataac gaagtcattc cagggcctca acaatggcc tatggaggac    1020 gtggtccgtg ggaacatctt cctgaggtag gagatcagcg cctagctgcg tcttctgtta    1080
gcactactta taaacctaac aaaaaagaaa aacttatgct aaacttgcta gacaaatgta    1140
aagagctaaa tctattagtt tatgaagact tagtagctaa ttgtcctgaa ctactcctta    1200
tgcttgaagg tcaaccagga ggggcacgcc ttatagaaca agtcttgggc atgcaccata    1260
ttaatgtttg ttctaacttt acagctctca catatctttt tcatctacat cctgttactt    1320
cgcttgactc agacaataaa gctttacagc ttttgttgat tcaaggctat aatcctctag    1380
ccgttggtca cgccctgtgc tgtgtcctga acaaacaatt cgggaaacaa acactgtttt    1440
gcttttacgg gcctgcctca acaggtaaaa caaatatggc caaggcaatc gtccaaggga    1500
ttagacttta tgggtgtgtt aatcatttga acaaaggatt tgtatttaat gactgcagac    1560
aacgcttagt tgtttggtgg gaggagtgct taatgcacca ggattgggtg aacctgcaa    1620 agtgtatctt gggcgggaca gaatgcagaa ttgacgtcaa gcatagagac agtgtacttt    1680
taactcaaac acctgtaatt atatccacta accacgatat ctacgcggtt gttggtggca    1740
attctgtttc tcatgttcac gcggctccat taaaagaaag agtgattcag ctaaattttta    1800 tgaaacaact tcctcaaaca tttggagaaa tcactgctac tgagattgca gctcttctac    1860
agtggtgttt caatgagtac gactgtactc tgacaggatt taaacaaaaa tggaatttag    1920
ataaaattcc aaactcattt cctcttgggg tcctttgtcc tactcattca caggactttta    1980 cacttcacga aaacggatac tgcactgatt gcggtggtta ccttcctcat agtgctgaca    2040
attctatgta cactgatcgc gcaagcgaaa ctagcacagg agacatcaca ccaagtaagt    2100
aaatacgcat gcgcaagtaa ttcttttact ttcacttcgc tattttttacc aatttttact    2160 tttaggtgac ttgggggatt cggacggaga agacaccgag cctgagacat cgcaagtgga    2220
ctattgtcca cccaagaaac gtcgtctaac tgctccagca agtcctccaa actcacctgc    2280
gagctctgta agtactatta ctttctttaa cacttggcac gcacagccac gtgacgaaga    2340
tgagctcagg gaatatgaaa gacaagcatc gctcctacaa aagaaaaggg agtccagaaa    2400
gaggggagag gaagagacac tggcagacaa ctcatcacag gagcaggagc cgcagcccga    2460
tccgacacag tggggagaga ggctcgggct catatcatca ggaacaccca atcagccacc    2520
tatcgtcttg cactgcttcg aagacctcag accaagtgat gaagacgagg gagagtacat    2580
cggggaaaaa agacaataga acaaatccat acactgtatt cagtcaacac agagcttcca    2640
atcctgaagc tccagggtgg tgtgggttct actggcactc tactcgcatt gctagagatg    2700
gtactaattc aatctttaat gaaatgaaac aacagtttca acagctacaa attgataata    2760
aaataggatg ggataacact agagaactat tgtttaatca aaagaaaaca ctagatcaaa    2820
aatacagaaa tatgttctgg cactttagaa ataactctga ttgtgaaaga tgtaattact    2880
```

```
gggatgatgt gtaccgtagg cacttagcta atgtttcctc acagacagaa gcagacgaga    2940
taactgacga ggaaatgctt tctgctgctg aaagcatgga agcagatgcc tccaattaag    3000
agacagccta gagggtgggt gctgcctgga tacagatatc ttgggccatt taatccactt    3060
gataacggtg aacctgtaaa taacgctgat cgcgctgctc aattacatga tcacgcctac    3120
tctgaactaa taaagagtgg taaaaatcca tacctgtatt tcaataaagc tgatgaaaaa    3180
ttcattgatg atctaaaaga cgattggtca attggtggaa ttattggatc cagttttttt    3240
aaaataaagc gcgccgtggc tcctgctctg ggaaataaag agagagccca aaaagacac    3300 ttttactttg ctaactcaaa taaggtgca aaaaaaacaa aaaaaagtga acctaaacca    3360
ggaacctcaa aaatgtctga cactgacatt caagaccaac aacctgatac tgtggacgca    3420
ccacagaacg cctcaggggg aggaacagga agtattggag gaggaaaagg atctggtgtg    3480
gggatttcca ctggagggtg ggtcggaggt tctcactttt cagacaaata tgtggttact    3540
aaaaacacaa gacaatttat aaccacaatt cagaatggtc acctctacaa aacagaggcc    3600
attgaaacaa caaaccaaag tggaaaatca cagcgctgcg tcacaactcc atggacatac    3660
tttaacttta atcaatacag ctgtcacttc tcaccacaag attggcagcg ccttacaaat    3720
gaatataagc gcttcagacc taaagcaatg caagtaaaga tttacaactt gcaaataaaa    3780
caaatacttt caaatggtgc tgacacaaca tacaacaatg acctcacagc tggcgttcac    3840
atcttttgtg atggagagca tgcttaccca aatgcatctc atccatggga tgaggacgtc    3900
atgcctgatc ttccatacaa gacctggaaa cttttttcaat atggatatat tcctattgaa    3960
aatgaactag cagatcttga tggaaatgca gctggaggca atgctacaga aaaagcactt    4020
ctgtatcaga tgcctttttt tctacttgaa aacagtgacc accaagtact tagaactggt    4080
gagagcactg aatttacttt taactttgac tgtgaatggg ttaataatga aagagcatac    4140
attcctcctg gattgatgtt caatccaaaa gttccaacaa gaagagttca gtacataaga    4200
caaaacggaa gcacagcagc cagcacaggc agaattcagc atactcaaa accaacaagc    4260 tggatgacag gacctggcct gctcagtgca cagagagtag gaccacagtc atcagacact    4320
gctccattca tggtttgcac taacccagaa ggaacacaca taaacacagg tgctgcagga    4380
tttggatctg gctttgatcc tccaagcgga tgtctggcac caactaacct agaatacaaa    4440
cttcagtggt accagacacc agaaggaaca ggaaataatg aaacataat tgcaaaccca    4500 tcactctcaa tgcttagaga ccaactccta tacaaggaa accagaccac atacaatcta    4560
gtgggggaca tatggatgtt tccaaatcaa gtctgggaca gatttcctat caccagaaa    4620 aatccaatct ggtgcaaaaa accaagggct gacaaacaca caatcatgga tccatttgat    4680
ggatccattg caatggatca tcctccaggc actatttta taaaaatggc aaaaattcca    4740
gtaccaactg caacaaatgc agactcatat ctaaacatat actgtactgg acaagtcagc    4800
tgtgaaattg tatgggaagt agaaagatac gcaacaaaga actggcgtcc agaaagaaga    4860
catactgcac tcgggatgtc actgggagga gagagcaact acacgcctac ataccacgtg    4920
gatccaacag gagcatacat ccagcccacg tcatatgatc agtgtatgcc agtaaaaaca    4980
aacatcaata agtgttgta atcttataag cctcttttt gcttctgctt acaagttcct    5040
cctcaatgga caagcggaaa gtgaagggtg actgtagtcc tgagctcatg ggttcaagac    5100
cacagcccga tggtagtggt gttaccgtct cgaacctagc cgacagccct tgtacattgt    5160 gggggggagct gttttgtttg cttatgcaat cgcgaaactc tatatctttt aatgtgt      5217
```

<210> SEQ ID NO 2

<211> LENGTH: 5299
<212> TYPE: DNA
<213> ORGANISM: Human bocavirus
<220> FEATURE:
<223> OTHER INFORMATION: Human bocavirus ST2 genomic DNA

<400> SEQUENCE: 2

| | | | | |
|---|---|---|---|---|
| gccggcagac | atattggatt | ccaagatggc | gtctgtacaa | ccacgtcaca | tataaaataa | 60 |
| taaatattca | caaggaggag | tggttatatg | atgtaatcca | taaccactcc | caggaaatga | 120 |
| cgtatgatag | ccaatcagaa | ttgagtatta | aacctatata | agctgctgca | cttcctgatt | 180 |
| caatcagact | gcatccggtc | tccggcgagt | gaacatctct | ggaaaaagct | ccacgcttgt | 240 |
| ggtgagtcta | ctatggcttt | caatcctcct | gtgattagag | ctttttctca | acctgctttt | 300 |
| acttatgtct | tcaaatttcc | atatccacaa | tggaaagaaa | agaatggct | gcttcatgca | 360 |
| cttttagctc | atggaactga | acaatctatg | atacaattaa | gaaactgcgc | tcctcatccg | 420 |
| gatgaagaca | taatccgtga | tgacttgctt | atttctttag | aagatcgcca | ttttggggct | 480 |
| gttctctgca | aggctgttta | catggcaaca | actactctca | tgtcacacaa | acaaaggaat | 540 |
| atgtttcctc | gttgtgacat | catagttcag | tctgagctag | agagaaaaa | cttacactgc | 600 |
| catattatag | ttgggggaga | aggactaagc | aagaggaatg | ctaaatcatc | ctgtgctcag | 660 |
| ttctatggtt | taatactagc | tgagataatt | caacgctgca | aatctcttct | ggctacacgt | 720 |
| cctttttgaac | ctgaggaggc | tgacatattt | cacactctaa | aaaaggctga | gcgagaggca | 780 |
| tggggtggag | ttactggcgg | caacatgcag | atccttcaat | atagagatcg | cagaggagac | 840 |
| cttcatgcac | aaacagtgga | tcctcttcgc | ttcttcaaaa | actaccttt | acctaaaaat | 900 |
| agatgtattt | catcttacag | caaacctgat | gtttgtactt | ctcctgacaa | ctggttcatt | 960 |
| ttagctgaaa | aaacttactc | tcacactctt | attaacgggc | tgccgcttcc | agaacattac | 1020 |
| agaaaaaact | accacgcaac | cctagataac | gaagtcattc | cagggcctca | aacaatggcc | 1080 |
| tatgaggac | gtggtccgtg | ggaacatctt | cctgaggtag | gagatcagcg | cctagctgcg | 1140 |
| tcttctgtta | gcactactta | taaacctaac | aaaaaagaaa | aacttatgct | aaacttgcta | 1200 |
| gacaaatgta | aagagctaaa | tctattagtt | tatgaagact | tagtagctaa | ttgtcctgaa | 1260 |
| ctactcctta | tgcttgaagg | tcaaccagga | ggggcacgcc | ttatagaaca | agtcttgggc | 1320 |
| atgcaccata | ttaatgtttg | ttctaacttt | acagctctca | catatctttt | tcatctacat | 1380 |
| cctgttactt | cgcttgactc | agacaataaa | gctttacagc | ttttgttgat | tcaaggctat | 1440 |
| aatcctctag | ccgttggtca | cgccctgtgc | tgtgtcctga | acaaacaatt | cgggaaacaa | 1500 |
| aacactgttt | gcttttacgg | gcctgcctca | acaggtaaaa | caaatatggc | caaggcaatc | 1560 |
| gtccaaggga | ttagactta | tgggtgtgtt | aatcatttga | acaaaggatt | tgtatttaat | 1620 |
| gactgcagac | aacgcctagt | tgtttggtgg | gaggagtgct | taatgcacca | ggattgggtg | 1680 |
| gaacctgcaa | agtgtatctt | gggcgggaca | gaatgcagaa | ttgacgtcaa | gcatagagac | 1740 |
| agtgtacttt | taactcaaac | acctgtaatt | atatccacta | accacgatat | ctacgcggtt | 1800 |
| gttggtggca | attctgtttc | tcatgttcac | gcggctccat | aaaagaaag | agtgattcag | 1860 |
| ctaaatttta | tgaaacaact | tcctcaaaca | tttggagaaa | tcactgctac | tgagattgca | 1920 |
| gctcttctac | agtggtgttt | caatgagtac | gactgtactc | tgcacaggatt | taaacaaaaa | 1980 |
| tggaatttag | ataaaattcc | aaactcattt | cctcttgggg | tcctttgtcc | tactcattca | 2040 |
| caggacttta | cacttcacga | aaacggatac | tgcactgatt | gcgtggtta | ccttcctcat | 2100 |
| agtgctgaca | attctatgta | cactgatcgc | gcaagcgaaa | ctagcacagg | agacatcaca | 2160 |

-continued

```
ccaagtaagt aaatacgcat gcgcaagtaa ttcttttact ttcacttcgc tattttttacc    2220
aatttttact tttaggtgac ttgggggatt cggacggaga agacaccgag cctgagacat    2280
cgcaagtgga ctattgtcca cccaagaaac gtcgtctaac tgctccagca agtcctccaa    2340
actcacctgc gagctctgta agtactatta ctttctttaa cacttggcac gcacagccac    2400
gtgacgaaga tgagctcagg gaatatgaaa gacaagcatc gctcctacaa aagaaaaggg    2460
agtccagaaa gaggggagag gaagagacac tggcagacaa ctcatcacag gagcaggagc    2520
cgcagcccga tccgacacag tggggagaga ggctcgggct catatcatca ggaacaccca    2580
atcagccacc tatcgtcttg cactgcttcg aagacctcag accaagtgat gaagacgagg    2640
gagagtacat cggggaaaaa agacaataga acaaatccat acactgtatt cagtcaacac    2700
agagcttcca atcctgaagc tccagggtgg tgtgggttct actggcactc tactcgcatt    2760
gctagagatg gtactaattc aatctttaat gaaatgaaac aacagtttca caactacaa    2820
attgataata aaataggatg ggataacact agagaactat tgtttaatca aaagaaaaca    2880
ctagatcaaa aatacagaaa tatgttctgg cactttagaa ataactctga ttgtgaaaga    2940
tgtaattact gggatgatgt gtaccgtaga cacttagcta atgtttcctc acagacagaa    3000
gcagacgaga taactgacga ggaaatgctt tctgctgctg aaagcatgga agcagatgcc    3060
tccaattaag agacagccta gagggtgggt gctgcctgga tacagatatc ttgggccatt    3120
taatccactt gataacggtg aacctgtaaa taacgctgat cgcgctgctc aattacatga    3180
tcacgcctac tctgaactaa taaagagtgg taaaaatcca tacctgtatt tcaataaagc    3240
tgatgaaaaa ttcattgatg atctaaaaga cgattggtca attggtggaa ttattggatc    3300
cagttttttt aaaataaagc gcgccgtggc tcctgctctg gaaataaag agagagccca    3360
aaaaagacac ttttactttg ctaactcaaa taaaggtgca aaaaaaacaa aaaaaagtga    3420
acctaaacca ggaaccctcaa aaatgtctga cactgacatt caagaccaac aacctgatac    3480
tgtggacgca ccacaaaaca cctcaggggg aggaacagga agtattggag gaggaaaagg    3540
atctggtgtg gggatttcca ctggagggtg ggtcggaggt tctcactttt cagacaaata    3600
tgtggttact aaaaacacaa gacaatttat aaccacaatt cagaatggtc acctctacaa    3660
aacagaggcc attgaaacaa caaaccaaag tggaaaatca cagcgctgcg tcacaactcc    3720
atggacatac tttaactttta atcaatacag ctgtcacttc tcaccacagg attggcagcg    3780
ccttacaaat gaatataagc gcttcagacc taaagcaatg caagtaaaga tttacaactt    3840
gcaaataaaa caaatacttt caaatggtgc tgacacaaca tacaacaatg acctcacagc    3900
tggcgttcac atcttttgtg atggagagca tgcttaccca aatgcatctc atccatggga    3960
tgaggacgtc atgcctgatc ttccatacaa gacctggaaa ctttttcaat atggatatat    4020
tcctattgaa aatgaactcg cagatcttga tggaaatgca gctggaggca atgctacaga    4080
aaaagcactt ctgtatcaga tgccttttttt tctacttgaa aacagtgacc accaagtact    4140
tagaactggt gagagcactg aatttacttt taactttgac tgtgaatggg ttaacaatga    4200
aagagcatac attcctcctg gactaatgtt taatccaaaa gtcccaacaa gaagagttca    4260
gtacataaga caaaacggaa gcacagcagc cagcacaggc agaattcagc catactcaaa    4320
accaacaagc tggatgacag gacctggcct gctcagtgca caagagtag gaccacagtc    4380
atcagacact gctccattca tggtttgcac taacccagaa ggaacacaca taaacacagg    4440
tgctgcagga tttggatctg gctttgatcc tccaaacgga tgtctggcac caactaacct    4500
agaatacaaa cttcagtggt accagacacc agaaggaaca ggaaataatg gaaacataat    4560
```

```
tgcaaaccca tcactctcaa tgcttagaga ccaactccta tacaaaggaa accaaaccac   4620
atacaatcta gtgggggaca tatggatgtt tccaaatcaa gtctgggaca gatttcctat   4680
caccagagaa atccaatct  ggtgcaaaaa accaagggct gacaaacaca caatcatgga   4740
tccatttgat ggatcaattg caatggatca tcctccaggc actatttta  taaaaatggc   4800 aaaaattcca gttccaactg cctcaaatgc agactcatac ctaaacatat actgtactgg   4860
acaagtcagc tgtgaaattg tatgggaggt agaaagatac gcaacaaaga actggcgtcc   4920
agaaagaaga catactgcac tcgggatgtc actgggagga gagagcaact acacgcctac   4980
ataccacgtg gatccaacag gagcatacat ccagcccacg tcatatgatc agtgtatgcc   5040
agtaaaaaca aacatcaata aagtgttgta atcttataag cctctttttt gcttctgctt   5100
acaagttcct cctcaatgga caagcggaaa gtgaagggtg actgtagtcc tgagctcatg   5160
ggttcaagac cacagcccga tggtagtggt gttaccgtct cgaacctagc cgacagccct   5220
tgtacattgt gggggagct  gttttgtttg cttatgcaat cgcgaaactc tatatctttt   5280
aatgtgttgt tgttgtaca                                                5299
```

<210> SEQ ID NO 3
<211> LENGTH: 639
<212> TYPE: PRT
<213> ORGANISM: Human bocavirus
<220> FEATURE:
<223> OTHER INFORMATION: Human bocavirus NS1 polypeptide encoded by nt
      183-2101 of SEQ ID NO: 1 and nt 253-2172 of SEQ ID NO: 2

<400> SEQUENCE: 3

```
Met Ala Phe Asn Pro Pro Val Ile Arg Ala Phe Ser Gln Pro Ala Phe
1               5                   10                  15

Thr Tyr Val Phe Lys Phe Pro Tyr Pro Gln Trp Lys Glu Lys Glu Trp
            20                  25                  30

Leu Leu His Ala Leu Leu Ala His Gly Thr Glu Gln Ser Met Ile Gln
        35                  40                  45

Leu Arg Asn Cys Ala Pro His Pro Asp Glu Asp Ile Ile Arg Asp Asp
    50                  55                  60

Leu Leu Ile Ser Leu Glu Asp Arg His Phe Gly Ala Val Leu Cys Lys
65                  70                  75                  80

Ala Val Tyr Met Ala Thr Thr Thr Leu Met Ser His Lys Gln Arg Asn
                85                  90                  95

Met Phe Pro Arg Cys Asp Ile Ile Val Gln Ser Glu Leu Gly Glu Lys
            100                 105                 110

Asn Leu His Cys His Ile Ile Val Gly Gly Glu Gly Leu Ser Lys Arg
        115                 120                 125

Asn Ala Lys Ser Ser Cys Ala Gln Phe Tyr Gly Leu Ile Leu Ala Glu
    130                 135                 140

Ile Ile Gln Arg Cys Lys Ser Leu Leu Ala Thr Arg Pro Phe Glu Pro
145                 150                 155                 160

Glu Glu Ala Asp Ile Phe His Thr Leu Lys Lys Ala Glu Arg Glu Ala
                165                 170                 175

Trp Gly Gly Val Thr Gly Gly Asn Met Gln Ile Leu Gln Tyr Arg Asp
            180                 185                 190

Arg Arg Gly Asp Leu His Ala Gln Thr Val Asp Pro Leu Arg Phe Phe
        195                 200                 205

Lys Asn Tyr Leu Leu Pro Lys Asn Arg Cys Ile Ser Ser Tyr Ser Lys
    210                 215                 220

Pro Asp Val Cys Thr Ser Pro Asp Asn Trp Phe Ile Leu Ala Glu Lys
```

```
               225                 230                 235                 240

Thr Tyr Ser His Thr Leu Ile Asn Gly Leu Pro Leu Pro Glu His Tyr
                        245                 250                 255

Arg Lys Asn Tyr His Ala Thr Leu Asp Asn Glu Val Ile Pro Gly Pro
                        260                 265                 270

Gln Thr Met Ala Tyr Gly Gly Arg Gly Pro Trp Glu His Leu Pro Glu
                        275                 280                 285

Val Gly Asp Gln Arg Leu Ala Ala Ser Ser Val Ser Thr Thr Tyr Lys
                    290                 295                 300

Pro Asn Lys Lys Glu Lys Leu Met Leu Asn Leu Leu Asp Lys Cys Lys
        305                 310                 315                 320

Glu Leu Asn Leu Leu Val Tyr Glu Asp Leu Val Ala Asn Cys Pro Glu
                        325                 330                 335

Leu Leu Leu Met Leu Glu Gly Gln Pro Gly Gly Ala Arg Leu Ile Glu
                        340                 345                 350

Gln Val Leu Gly Met His His Ile Asn Val Cys Ser Asn Phe Thr Ala
                    355                 360                 365

Leu Thr Tyr Leu Phe His Leu His Pro Val Thr Ser Leu Asp Ser Asp
            370                 375                 380

Asn Lys Ala Leu Gln Leu Leu Ile Gln Gly Tyr Asn Pro Leu Ala
        385                 390                 395                 400

Val Gly His Ala Leu Cys Cys Val Leu Asn Lys Gln Phe Gly Lys Gln
                        405                 410                 415

Asn Thr Val Cys Phe Tyr Gly Pro Ala Ser Thr Gly Lys Thr Asn Met
                    420                 425                 430

Ala Lys Ala Ile Val Gln Gly Ile Arg Leu Tyr Gly Cys Val Asn His
                    435                 440                 445

Leu Asn Lys Gly Phe Val Phe Asn Asp Cys Arg Gln Arg Leu Val Val
            450                 455                 460

Trp Trp Glu Glu Cys Leu Met His Gln Asp Trp Val Glu Pro Ala Lys
        465                 470                 475                 480

Cys Ile Leu Gly Gly Thr Glu Cys Arg Ile Asp Val Lys His Arg Asp
                        485                 490                 495

Ser Val Leu Leu Thr Gln Thr Pro Val Ile Ser Thr Asn His Asp
                    500                 505                 510

Ile Tyr Ala Val Val Gly Gly Asn Ser Val Ser His Val His Ala Ala
                    515                 520                 525

Pro Leu Lys Glu Arg Val Ile Gln Leu Asn Phe Met Lys Gln Leu Pro
            530                 535                 540

Gln Thr Phe Gly Glu Ile Thr Ala Thr Glu Ile Ala Ala Leu Leu Gln
        545                 550                 555                 560

Trp Cys Phe Asn Glu Tyr Asp Cys Thr Leu Thr Gly Phe Lys Gln Lys
                        565                 570                 575

Trp Asn Leu Asp Lys Ile Pro Asn Ser Phe Pro Leu Gly Val Leu Cys
                    580                 585                 590

Pro Thr His Ser Gln Asp Phe Thr Leu His Glu Asn Gly Tyr Cys Thr
                    595                 600                 605

Asp Cys Gly Gly Tyr Leu Pro His Ser Ala Asp Asn Ser Met Tyr Thr
            610                 615                 620

Asp Arg Ala Ser Glu Thr Ser Thr Gly Asp Ile Thr Pro Ser Lys
        625                 630                 635

<210> SEQ ID NO 4
<211> LENGTH: 219
```

```
<212> TYPE: PRT
<213> ORGANISM: Human bocavirus
<220> FEATURE:
<223> OTHER INFORMATION: Human bocavirus NP-1 polypeptide encoded by nt
      2340-2999 of SEQ ID NO: 1 and nt 2410-3069 of SEQ ID NO: 2

<400> SEQUENCE: 4

Met Ser Ser Gly Asn Met Lys Asp Lys His Arg Ser Tyr Lys Arg Lys
1               5                   10                  15

Gly Ser Pro Glu Arg Gly Glu Arg Lys Arg His Trp Gln Thr Thr His
                20                  25                  30

His Arg Ser Arg Ser Arg Ser Pro Ile Arg His Ser Gly Glu Arg Gly
            35                  40                  45

Ser Gly Ser Tyr His Gln Glu His Pro Ile Ser His Leu Ser Ser Cys
        50                  55                  60

Thr Ala Ser Lys Thr Ser Asp Gln Val Met Lys Thr Arg Glu Ser Thr
65                  70                  75                  80

Ser Gly Lys Lys Asp Asn Arg Thr Asn Pro Tyr Thr Val Phe Ser Gln
                85                  90                  95

His Arg Ala Ser Asn Pro Glu Ala Pro Gly Trp Cys Gly Phe Tyr Trp
                100                 105                 110

His Ser Thr Arg Ile Ala Arg Asp Gly Thr Asn Ser Ile Phe Asn Glu
            115                 120                 125

Met Lys Gln Gln Phe Gln Gln Leu Gln Ile Asp Asn Lys Ile Gly Trp
        130                 135                 140

Asp Asn Thr Arg Glu Leu Leu Phe Asn Gln Lys Lys Thr Leu Asp Gln
145                 150                 155                 160

Lys Tyr Arg Asn Met Phe Trp His Phe Arg Asn Asn Ser Asp Cys Glu
                165                 170                 175

Arg Cys Asn Tyr Trp Asp Asp Val Tyr Arg Arg His Leu Ala Asn Val
                180                 185                 190

Ser Ser Gln Thr Glu Ala Asp Glu Ile Thr Asp Glu Glu Met Leu Ser
            195                 200                 205

Ala Ala Glu Ser Met Glu Ala Asp Ala Ser Asn
        210                 215

<210> SEQ ID NO 5
<211> LENGTH: 671
<212> TYPE: PRT
<213> ORGANISM: Human bocavirus
<220> FEATURE:
<223> OTHER INFORMATION: Human bocavirus ST1 VP1 polypeptide encoded by
      nt 2986-5001 of SEQ ID NO: 1

<400> SEQUENCE: 5

Met Pro Pro Ile Lys Arg Gln Pro Arg Gly Trp Val Leu Pro Gly Tyr
1               5                   10                  15

Arg Tyr Leu Gly Pro Phe Asn Pro Leu Asp Asn Gly Glu Pro Val Asn
                20                  25                  30

Asn Ala Asp Arg Ala Ala Gln Leu His Asp His Ala Tyr Ser Glu Leu
            35                  40                  45

Ile Lys Ser Gly Lys Asn Pro Tyr Leu Tyr Phe Asn Lys Ala Asp Glu
        50                  55                  60

Lys Phe Ile Asp Asp Leu Lys Asp Asp Trp Ser Ile Gly Gly Ile Ile
65                  70                  75                  80

Gly Ser Ser Phe Phe Lys Ile Lys Arg Ala Val Ala Pro Ala Leu Gly
                85                  90                  95

Asn Lys Glu Arg Ala Gln Lys Arg His Phe Tyr Phe Ala Asn Ser Asn
```

```
            100                 105                 110
Lys Gly Ala Lys Lys Thr Lys Lys Ser Glu Pro Lys Pro Gly Thr Ser
            115                 120                 125
Lys Met Ser Asp Thr Asp Ile Gln Asp Gln Pro Asp Thr Val Asp
            130                 135                 140
Ala Pro Gln Asn Ala Ser Gly Gly Thr Gly Ser Ile Gly Gly Gly
145                 150                 155                 160
Lys Gly Ser Gly Val Gly Ile Ser Thr Gly Gly Trp Val Gly Gly Ser
                165                 170                 175
His Phe Ser Asp Lys Tyr Val Val Thr Lys Asn Thr Arg Gln Phe Ile
                180                 185                 190
Thr Thr Ile Gln Asn Gly His Leu Tyr Lys Thr Glu Ala Ile Glu Thr
                195                 200                 205
Thr Asn Gln Ser Gly Lys Ser Gln Arg Cys Val Thr Thr Pro Trp Thr
                210                 215                 220
Tyr Phe Asn Phe Asn Gln Tyr Ser Cys His Phe Ser Pro Gln Asp Trp
225                 230                 235                 240
Gln Arg Leu Thr Asn Glu Tyr Lys Arg Phe Arg Pro Lys Ala Met Gln
                245                 250                 255
Val Lys Ile Tyr Asn Leu Gln Ile Lys Gln Ile Leu Ser Asn Gly Ala
                260                 265                 270
Asp Thr Thr Tyr Asn Asn Asp Leu Thr Ala Gly Val His Ile Phe Cys
                275                 280                 285
Asp Gly Glu His Ala Tyr Pro Asn Ala Ser His Pro Trp Asp Glu Asp
                290                 295                 300
Val Met Pro Asp Leu Pro Tyr Lys Thr Trp Lys Leu Phe Gln Tyr Gly
305                 310                 315                 320
Tyr Ile Pro Ile Glu Asn Glu Leu Ala Asp Leu Asp Gly Asn Ala Ala
                325                 330                 335
Gly Gly Asn Ala Thr Glu Lys Ala Leu Leu Tyr Gln Met Pro Phe Phe
                340                 345                 350
Leu Leu Glu Asn Ser Asp His Gln Val Leu Arg Thr Gly Glu Ser Thr
                355                 360                 365
Glu Phe Thr Phe Asn Phe Asp Cys Glu Trp Val Asn Asn Glu Arg Ala
                370                 375                 380
Tyr Ile Pro Pro Gly Leu Met Phe Asn Pro Lys Val Pro Thr Arg Arg
385                 390                 395                 400
Val Gln Tyr Ile Arg Gln Asn Gly Ser Thr Ala Ala Ser Thr Gly Arg
                405                 410                 415
Ile Gln Pro Tyr Ser Lys Pro Thr Ser Trp Met Thr Gly Pro Gly Leu
                420                 425                 430
Leu Ser Ala Gln Arg Val Gly Pro Gln Ser Ser Asp Thr Ala Pro Phe
                435                 440                 445
Met Val Cys Thr Asn Pro Glu Gly Thr His Ile Asn Thr Gly Ala Ala
                450                 455                 460
Gly Phe Gly Ser Gly Phe Asp Pro Pro Ser Gly Cys Leu Ala Pro Thr
465                 470                 475                 480
Asn Leu Glu Tyr Lys Leu Gln Trp Tyr Gln Thr Pro Glu Gly Thr Gly
                485                 490                 495
Asn Asn Gly Asn Ile Ile Ala Asn Pro Ser Leu Ser Met Leu Arg Asp
                500                 505                 510
Gln Leu Leu Tyr Lys Gly Asn Gln Thr Thr Tyr Asn Leu Val Gly Asp
                515                 520                 525
```

```
Ile Trp Met Phe Pro Asn Gln Val Trp Asp Arg Phe Pro Ile Thr Arg
        530                 535                 540

Glu Asn Pro Ile Trp Cys Lys Lys Pro Arg Ala Asp Lys His Thr Ile
545                 550                 555                 560

Met Asp Pro Phe Asp Gly Ser Ile Ala Met Asp His Pro Pro Gly Thr
                565                 570                 575

Ile Phe Ile Lys Met Ala Lys Ile Pro Val Pro Thr Ala Thr Asn Ala
                580                 585                 590

Asp Ser Tyr Leu Asn Ile Tyr Cys Thr Gly Gln Val Ser Cys Glu Ile
            595                 600                 605

Val Trp Glu Val Glu Arg Tyr Ala Thr Lys Asn Trp Arg Pro Glu Arg
        610                 615                 620

Arg His Thr Ala Leu Gly Met Ser Leu Gly Gly Glu Ser Asn Tyr Thr
625                 630                 635                 640

Pro Thr Tyr His Val Asp Pro Thr Gly Ala Tyr Ile Gln Pro Thr Ser
                645                 650                 655

Tyr Asp Gln Cys Met Pro Val Lys Thr Asn Ile Asn Lys Val Leu
                660                 665                 670

<210> SEQ ID NO 6
<211> LENGTH: 542
<212> TYPE: PRT
<213> ORGANISM: Human bocavirus
<220> FEATURE:
<223> OTHER INFORMATION: Human bocavirus ST1 VP2 polypeptide encoded by
      nt 3373-5001 of SEQ ID NO: 1

<400> SEQUENCE: 6

Met Ser Asp Thr Asp Ile Gln Asp Gln Gln Pro Asp Thr Val Asp Ala
1               5                   10                  15

Pro Gln Asn Ala Ser Gly Gly Thr Gly Ser Ile Gly Gly Gly Gly Lys
            20                  25                  30

Gly Ser Gly Val Gly Ile Ser Thr Gly Gly Trp Val Gly Gly Ser His
        35                  40                  45

Phe Ser Asp Lys Tyr Val Val Thr Lys Asn Thr Arg Gln Phe Ile Thr
    50                  55                  60

Thr Ile Gln Asn Gly His Leu Tyr Lys Thr Glu Ala Ile Glu Thr Thr
65                  70                  75                  80

Asn Gln Ser Gly Lys Ser Gln Arg Cys Val Thr Thr Pro Trp Thr Tyr
                85                  90                  95

Phe Asn Phe Asn Gln Tyr Ser Cys His Phe Ser Pro Asp Trp Gln
            100                 105                 110

Arg Leu Thr Asn Glu Tyr Lys Arg Phe Arg Pro Lys Ala Met Gln Val
        115                 120                 125

Lys Ile Tyr Asn Leu Gln Ile Lys Gln Ile Leu Ser Asn Gly Ala Asp
    130                 135                 140

Thr Thr Tyr Asn Asn Asp Leu Thr Ala Gly Val His Ile Phe Cys Asp
145                 150                 155                 160

Gly Glu His Ala Tyr Pro Asn Ala Ser His Pro Trp Asp Glu Asp Val
                165                 170                 175

Met Pro Asp Leu Pro Tyr Lys Thr Trp Lys Leu Phe Gln Tyr Gly Tyr
            180                 185                 190

Ile Pro Ile Glu Asn Glu Leu Ala Asp Leu Asp Gly Asn Ala Ala Gly
        195                 200                 205

Gly Asn Ala Thr Glu Lys Ala Leu Leu Tyr Gln Met Pro Phe Phe Leu
    210                 215                 220
```

-continued

```
Leu Glu Asn Ser Asp His Gln Val Leu Arg Thr Gly Glu Ser Thr Glu
225                 230                 235                 240

Phe Thr Phe Asn Phe Asp Cys Glu Trp Val Asn Asn Glu Arg Ala Tyr
                245                 250                 255

Ile Pro Pro Gly Leu Met Phe Asn Pro Lys Val Pro Thr Arg Arg Val
            260                 265                 270

Gln Tyr Ile Arg Gln Asn Gly Ser Thr Ala Ala Ser Thr Gly Arg Ile
        275                 280                 285

Gln Pro Tyr Ser Lys Pro Thr Ser Trp Met Thr Gly Pro Gly Leu Leu
    290                 295                 300

Ser Ala Gln Arg Val Gly Pro Gln Ser Ser Asp Thr Ala Pro Phe Met
305                 310                 315                 320

Val Cys Thr Asn Pro Glu Gly Thr His Ile Asn Thr Gly Ala Ala Gly
                325                 330                 335

Phe Gly Ser Gly Phe Asp Pro Pro Ser Gly Cys Leu Ala Pro Thr Asn
            340                 345                 350

Leu Glu Tyr Lys Leu Gln Trp Tyr Gln Thr Pro Glu Gly Thr Gly Asn
        355                 360                 365

Asn Gly Asn Ile Ile Ala Asn Pro Ser Leu Ser Met Leu Arg Asp Gln
    370                 375                 380

Leu Leu Tyr Lys Gly Asn Gln Thr Thr Tyr Asn Leu Val Gly Asp Ile
385                 390                 395                 400

Trp Met Phe Pro Asn Gln Val Trp Asp Arg Phe Pro Ile Thr Arg Glu
                405                 410                 415

Asn Pro Ile Trp Cys Lys Lys Pro Arg Ala Asp Lys His Thr Ile Met
            420                 425                 430

Asp Pro Phe Asp Gly Ser Ile Ala Met Asp His Pro Pro Gly Thr Ile
        435                 440                 445

Phe Ile Lys Met Ala Lys Ile Pro Val Pro Thr Ala Thr Asn Ala Asp
    450                 455                 460

Ser Tyr Leu Asn Ile Tyr Cys Thr Gly Gln Val Ser Cys Glu Ile Val
465                 470                 475                 480

Trp Glu Val Glu Arg Tyr Ala Thr Lys Asn Trp Arg Pro Glu Arg Arg
                485                 490                 495

His Thr Ala Leu Gly Met Ser Leu Gly Gly Glu Ser Asn Tyr Thr Pro
            500                 505                 510

Thr Tyr His Val Asp Pro Thr Gly Ala Tyr Ile Gln Pro Thr Ser Tyr
        515                 520                 525

Asp Gln Cys Met Pro Val Lys Thr Asn Ile Asn Lys Val Leu
    530                 535                 540

<210> SEQ ID NO 7
<211> LENGTH: 671
<212> TYPE: PRT
<213> ORGANISM: Human bocavirus
<220> FEATURE:
<223> OTHER INFORMATION: Human bocavirus ST2 VP1 polypeptide encoded by
      nt 3056-5071 of SEQ ID NO: 2

<400> SEQUENCE: 7

Met Pro Pro Ile Lys Arg Gln Pro Arg Gly Trp Val Leu Pro Gly Tyr
1               5                   10                  15

Arg Tyr Leu Gly Pro Phe Asn Pro Leu Asp Asn Gly Glu Pro Val Asn
            20                  25                  30

Asn Ala Asp Arg Ala Ala Gln Leu His Asp His Ala Tyr Ser Glu Leu
        35                  40                  45
```

```
Ile Lys Ser Gly Lys Asn Pro Tyr Leu Tyr Phe Asn Lys Ala Asp Glu
 50                  55                  60
Lys Phe Ile Asp Asp Leu Lys Asp Asp Trp Ser Ile Gly Gly Ile Ile
 65                  70                  75                  80
Gly Ser Ser Phe Phe Lys Ile Lys Arg Ala Val Ala Pro Ala Leu Gly
                 85                  90                  95
Asn Lys Glu Arg Ala Gln Lys Arg His Phe Tyr Phe Ala Asn Ser Asn
             100                 105                 110
Lys Gly Ala Lys Lys Thr Lys Lys Ser Glu Pro Lys Pro Gly Thr Ser
         115                 120                 125
Lys Met Ser Asp Thr Asp Ile Gln Asp Gln Pro Asp Thr Val Asp
 130                 135                 140
Ala Pro Gln Asn Thr Ser Gly Gly Thr Gly Ser Ile Gly Gly Gly
 145                 150                 155                 160
Lys Gly Ser Gly Val Gly Ile Ser Thr Gly Gly Trp Val Gly Ser
                 165                 170                 175
His Phe Ser Asp Lys Tyr Val Val Thr Lys Asn Thr Arg Gln Phe Ile
                 180                 185                 190
Thr Thr Ile Gln Asn Gly His Leu Tyr Lys Thr Glu Ala Ile Glu Thr
                 195                 200                 205
Thr Asn Gln Ser Gly Lys Ser Gln Arg Cys Val Thr Thr Pro Trp Thr
 210                 215                 220
Tyr Phe Asn Phe Asn Gln Tyr Ser Cys His Phe Ser Pro Gln Asp Trp
 225                 230                 235                 240
Gln Arg Leu Thr Asn Glu Tyr Lys Arg Phe Arg Pro Lys Ala Met Gln
                 245                 250                 255
Val Lys Ile Tyr Asn Leu Gln Ile Lys Gln Ile Leu Ser Asn Gly Ala
                 260                 265                 270
Asp Thr Thr Tyr Asn Asn Asp Leu Thr Ala Gly Val His Ile Phe Cys
                 275                 280                 285
Asp Gly Glu His Ala Tyr Pro Asn Ala Ser His Pro Trp Asp Glu Asp
         290                 295                 300
Val Met Pro Asp Leu Pro Tyr Lys Thr Trp Lys Leu Phe Gln Tyr Gly
 305                 310                 315                 320
Tyr Ile Pro Ile Glu Asn Glu Leu Ala Asp Leu Asp Gly Asn Ala Ala
                 325                 330                 335
Gly Gly Asn Ala Thr Glu Lys Ala Leu Leu Tyr Gln Met Pro Phe Phe
             340                 345                 350
Leu Leu Glu Asn Ser Asp His Gln Val Leu Arg Thr Gly Glu Ser Thr
             355                 360                 365
Glu Phe Thr Phe Asn Phe Asp Cys Glu Trp Val Asn Asn Glu Arg Ala
     370                 375                 380
Tyr Ile Pro Pro Gly Leu Met Phe Asn Pro Lys Val Pro Thr Arg Arg
 385                 390                 395                 400
Val Gln Tyr Ile Arg Gln Asn Gly Ser Thr Ala Ala Ser Thr Gly Arg
                 405                 410                 415
Ile Gln Pro Tyr Ser Lys Pro Thr Ser Trp Met Thr Gly Pro Gly Leu
                 420                 425                 430
Leu Ser Ala Gln Arg Val Gly Pro Gln Ser Ser Asp Thr Ala Pro Phe
         435                 440                 445
Met Val Cys Thr Asn Pro Glu Gly Thr His Ile Asn Thr Gly Ala Ala
     450                 455                 460
Gly Phe Gly Ser Gly Phe Asp Pro Pro Asn Gly Cys Leu Ala Pro Thr
 465                 470                 475                 480
```

```
Asn Leu Glu Tyr Lys Leu Gln Trp Tyr Gln Thr Pro Glu Gly Thr Gly
            485                 490                 495

Asn Asn Gly Asn Ile Ile Ala Asn Pro Ser Leu Ser Met Leu Arg Asp
            500                 505                 510

Gln Leu Leu Tyr Lys Gly Asn Gln Thr Thr Tyr Asn Leu Val Gly Asp
            515                 520                 525

Ile Trp Met Phe Pro Asn Gln Val Trp Asp Arg Phe Pro Ile Thr Arg
            530                 535                 540

Glu Asn Pro Ile Trp Cys Lys Lys Pro Arg Ala Asp Lys His Thr Ile
545                 550                 555                 560

Met Asp Pro Phe Asp Gly Ser Ile Ala Met Asp His Pro Pro Gly Thr
            565                 570                 575

Ile Phe Ile Lys Met Ala Lys Ile Pro Val Pro Thr Ala Ser Asn Ala
            580                 585                 590

Asp Ser Tyr Leu Asn Ile Tyr Cys Thr Gly Gln Val Ser Cys Glu Ile
            595                 600                 605

Val Trp Glu Val Glu Arg Tyr Ala Thr Lys Asn Trp Arg Pro Glu Arg
            610                 615                 620

Arg His Thr Ala Leu Gly Met Ser Leu Gly Glu Ser Asn Tyr Thr
625                 630                 635                 640

Pro Thr Tyr His Val Asp Pro Thr Gly Ala Tyr Ile Gln Pro Thr Ser
            645                 650                 655

Tyr Asp Gln Cys Met Pro Val Lys Thr Asn Ile Asn Lys Val Leu
            660                 665                 670

<210> SEQ ID NO 8
<211> LENGTH: 542
<212> TYPE: PRT
<213> ORGANISM: Human bocavirus
<220> FEATURE:
<223> OTHER INFORMATION: Human bocavirus ST2 VP2 polypeptide encoded by
      nt 3343-5071 of SEQ ID NO: 2

<400> SEQUENCE: 8

Met Ser Asp Thr Asp Ile Gln Asp Gln Gln Pro Asp Thr Val Asp Ala
1               5                   10                  15

Pro Gln Asn Thr Ser Gly Gly Thr Gly Ser Ile Gly Gly Gly Lys
            20                  25                  30

Gly Ser Gly Val Gly Ile Ser Thr Gly Gly Trp Val Gly Gly Ser His
            35                  40                  45

Phe Ser Asp Lys Tyr Val Val Thr Lys Asn Thr Arg Gln Phe Ile Thr
50                  55                  60

Thr Ile Gln Asn Gly His Leu Tyr Lys Thr Glu Ala Ile Glu Thr Thr
65                  70                  75                  80

Asn Gln Ser Gly Lys Ser Gln Arg Cys Val Thr Thr Pro Trp Thr Tyr
            85                  90                  95

Phe Asn Phe Asn Gln Tyr Ser Cys His Phe Ser Pro Gln Asp Trp Gln
            100                 105                 110

Arg Leu Thr Asn Glu Tyr Lys Arg Phe Arg Pro Lys Ala Met Gln Val
            115                 120                 125

Lys Ile Tyr Asn Leu Gln Ile Lys Gln Ile Leu Ser Asn Gly Ala Asp
            130                 135                 140

Thr Thr Tyr Asn Asn Asp Leu Thr Ala Gly Val His Ile Phe Cys Asp
145                 150                 155                 160

Gly Glu His Ala Tyr Pro Asn Ala Ser His Pro Trp Asp Glu Asp Val
            165                 170                 175
```

```
Met Pro Asp Leu Pro Tyr Lys Thr Trp Lys Leu Phe Gln Tyr Gly Tyr
            180                 185                 190

Ile Pro Ile Glu Asn Glu Leu Ala Asp Leu Asp Gly Asn Ala Ala Gly
        195                 200                 205

Gly Asn Ala Thr Glu Lys Ala Leu Leu Tyr Gln Met Pro Phe Phe Leu
    210                 215                 220

Leu Glu Asn Ser Asp His Gln Val Leu Arg Thr Gly Glu Ser Thr Glu
225                 230                 235                 240

Phe Thr Phe Asn Phe Asp Cys Glu Trp Val Asn Asn Glu Arg Ala Tyr
                245                 250                 255

Ile Pro Pro Gly Leu Met Phe Asn Pro Lys Val Pro Thr Arg Arg Val
            260                 265                 270

Gln Tyr Ile Arg Gln Asn Gly Ser Thr Ala Ala Ser Thr Gly Arg Ile
        275                 280                 285

Gln Pro Tyr Ser Lys Pro Thr Ser Trp Met Thr Gly Pro Gly Leu Leu
    290                 295                 300

Ser Ala Gln Arg Val Gly Pro Gln Ser Ser Asp Thr Ala Pro Phe Met
305                 310                 315                 320

Val Cys Thr Asn Pro Glu Gly Thr His Ile Asn Thr Gly Ala Ala Gly
                325                 330                 335

Phe Gly Ser Gly Phe Asp Pro Pro Asn Gly Cys Leu Ala Pro Thr Asn
            340                 345                 350

Leu Glu Tyr Lys Leu Gln Trp Tyr Gln Thr Pro Glu Gly Thr Gly Asn
        355                 360                 365

Asn Gly Asn Ile Ile Ala Asn Pro Ser Leu Ser Met Leu Arg Asp Gln
    370                 375                 380

Leu Leu Tyr Lys Gly Asn Gln Thr Thr Tyr Asn Leu Val Gly Asp Ile
385                 390                 395                 400

Trp Met Phe Pro Asn Gln Val Trp Asp Arg Phe Pro Ile Thr Arg Glu
                405                 410                 415

Asn Pro Ile Trp Cys Lys Lys Pro Arg Ala Asp Lys His Thr Ile Met
            420                 425                 430

Asp Pro Phe Asp Gly Ser Ile Ala Met Asp His Pro Pro Gly Thr Ile
        435                 440                 445

Phe Ile Lys Met Ala Lys Ile Pro Val Pro Thr Ala Ser Asn Ala Asp
450                 455                 460

Ser Tyr Leu Asn Ile Tyr Cys Thr Gly Gln Val Ser Cys Glu Ile Val
465                 470                 475                 480

Trp Glu Val Glu Arg Tyr Ala Thr Lys Asn Trp Arg Pro Glu Arg Arg
                485                 490                 495

His Thr Ala Leu Gly Met Ser Leu Gly Gly Glu Ser Asn Tyr Thr Pro
            500                 505                 510

Thr Tyr His Val Asp Pro Thr Gly Ala Tyr Ile Gln Pro Thr Ser Tyr
        515                 520                 525

Asp Gln Cys Met Pro Val Lys Thr Asn Ile Asn Lys Val Leu
530                 535                 540

<210> SEQ ID NO 9
<211> LENGTH: 21
<212> TYPE: DNA
<213> ORGANISM: Artificial sequence
<220> FEATURE:
<223> OTHER INFORMATION: Synthetic sequence: Primer 188F

<400> SEQUENCE: 9
```

```
gagctctgta agtactatta c                                                21

<210> SEQ ID NO 10
<211> LENGTH: 21
<212> TYPE: DNA
<213> ORGANISM: Artificial sequence
<220> FEATURE:
<223> OTHER INFORMATION: Synthetic sequence: Primer 542R

<400> SEQUENCE: 10
ctctgtgttg actgaataca g                                                21
```

HUMAN *BOCAVIRUS* AND METHODS OF DIAGNOSIS AND TREATMENT

The present application is §371 application of PCT/EP2006/008074 filed 16 Aug. 2006 which claims priority to US Provisional Application 60/737,576 filed 17 Nov. 2005, the entire disclosure of each being incorporated by reference herein.

Parvoviruses are capable of systemic infection of humans and other animals. Parvoviruses require proliferating host cells in order to replicate, so infection of respiratory and gut epithelium, hematopoietic cells, and transplacental infection of fetuses are frequent characteristics of parvoviruses. Parvovirus infections can therefore be associated with fetal infection and spontaneous abortion. They are also associated with respiratory tract infections. Lower respiratory tract infections (LRTI) are a leading cause of hospitalization of infants and young children.

The Parvoviridae family ("parvoviruses") is divided into two subfamilies, Densovirinae infecting arthropods, and Parvovirinae, infecting birds and mammals. The viruses in the Parvovirinae subfamily have recently been reclassified into five genera by ICTV: Parvovirus, Erythrovirus, Dependovirus, Amdovirus and Bocavirus.

Previously known human parvoviruses are the well-known pathogen parvovirus B19 [1], including genotypes A6 and V9 (Erythrovirus), and the presumably apathogenic adeno-associated viruses (Dependovirus). Another virus isolate provisionally named human parvovirus 4 and detected in human blood was recently reported [2]. Its medical consequences are unknown.

Animal bocaviruses BPV (bovine parvovirus) and MVC (canine minute virus, or minute virus of canines) are associated with respiratory symptoms and enteritis of young animals. Systemic infection by BPV and MVC appears likely, and there are indications that fetal infection leading to fetal death may occur.

We have isolated and identified a new parvovirus. Specifically, the virus belongs to the Parvoviridae family, subfamily Parvovirinae, genus Bocavirus. We designate the virus "human bocavirus (HBoV)". We believe this is only the second reported parvovirus species pathogenic to humans (after B19), and is the first reported human virus of the genus Bocavirus.

HBoV is associated with respiratory tract infections in children, which are frequently sufficiently severe to result in hospitalization. Thus, this virus explains a proportion of acute infections in children, the cause of which was previously unknown. HBoV may also be associated with other clinical manifestations.

The DNA sequences of the HBoV genome, and its encoded polypeptides, are disclosed herein. HBoV nucleotide sequences SEQ ID NOS 1 to 8 are shown in the appended sequence listing. Isolated nucleic acid molecules comprising one or more of these sequences, or their complementary sequences or fragments thereof, are aspects of the present invention. The nucleic acid molecules may for example be DNA or RNA.

HBoV sequences can be used to produce diagnostic materials for identifying or demonstrating the presence of the virus in a sample. Specific binding members e.g. antibodies to HBoV polypeptides may be produced.

HBoV nucleic acids and polypeptides may also be used to produce vaccines against HBoV, which may be administered to individuals, especially humans, such as babies, infants and children.

Figure 1:
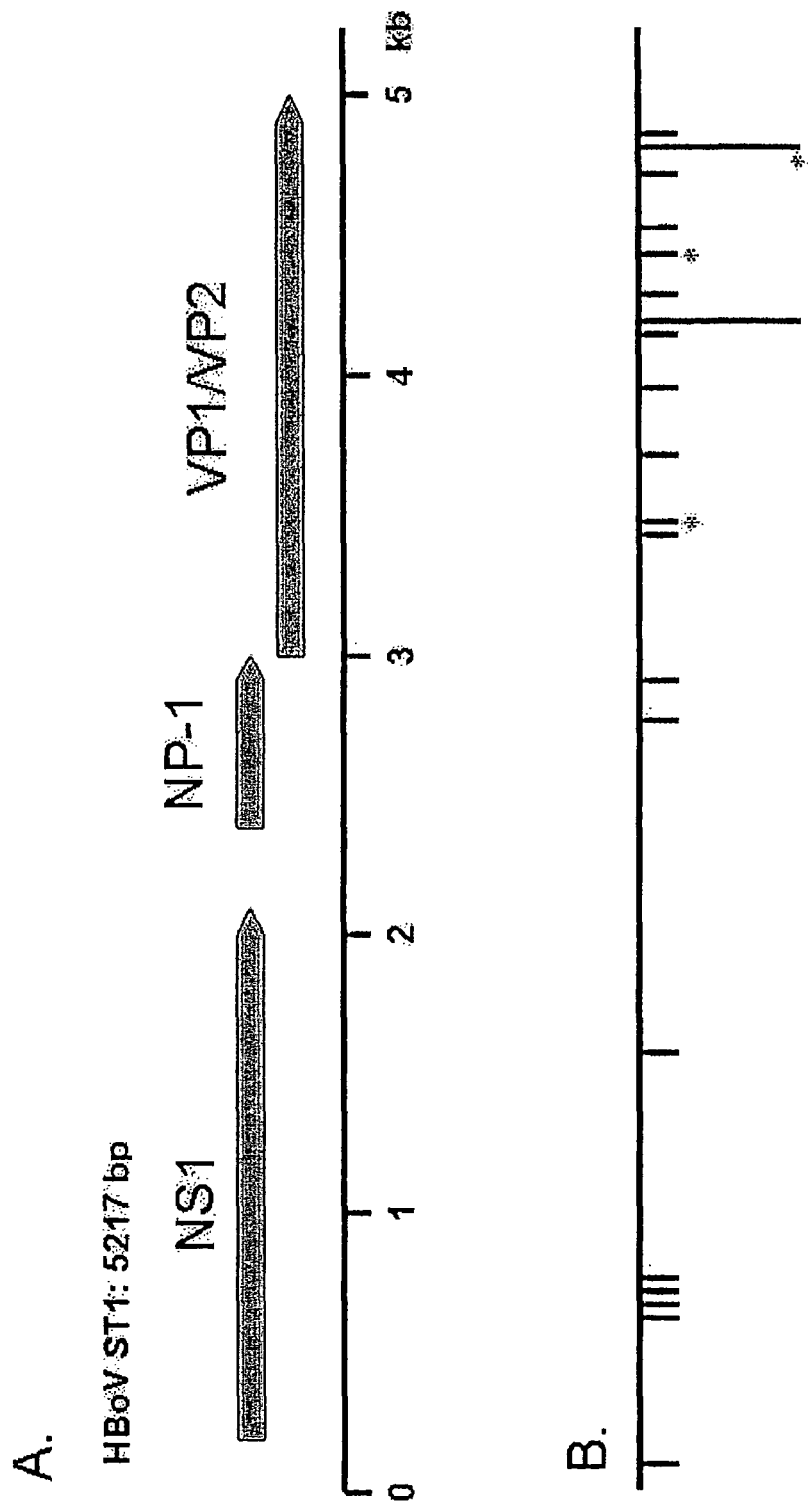
FIG. 1 Maps of the human bocavirus genome. A. Schematic map of isolate ST1 of HBoV showing the three open reading frames as arrows. They are: NS1, 1920 bp (183-2102), 639 a.a., NP-1, 660 bp (2340-2999), 219 a.a. and VP1/VP2, 2016 bp (2986-5001), 671 a.a. B. A map showing the location of the 26 nucleotide differences that were detected between two isolates of HBoV. The horizontal line represents the sequence of ST1, while each vertical line represents a nucleotide difference to ST2. In two cases where several differences were located close together, a longer vertical line representing four differences was used. The asterisks mark the three differences that resulted in a predicted amino acid change.

HBoV was identified from human respiratory tract samples using a system for large-scale molecular virus screening of clinical samples based on host DNA depletion, random PCR amplification, large-scale sequencing, and bioinformatics. Details of the methodology are described in [3] and [4], the contents of which are incorporated herein by reference. The samples included in the study were randomly selected nasopharyngeal aspirates submitted to Karolinska University Laboratory, Stockholm, Sweden for diagnostics of respiratory tract infections. Two pools of centrifuged, cell-free supernatants of anonymized nasopharyngeal aspirates were analyzed.

Parvovirus-like sequences were found in both libraries. They showed no significant similarity to database sequences at the nucleotide level in a BLAST search. However, the deduced amino acid sequence showed notable similarity with BPV and MVC, two related members of the Parvoviridae family, subfamily Parvovirinae, genus Bocavirus.

The individual source samples in the respective screening pool were identified by specific PCR targeting the sequence of the first detected clones. Using these samples as templates, we determined the complete coding consensus sequence of both index isolates: Stockholm 1 (ST1), 5217 nt, accession No DQ000495 [gi:66356128] and Stockholm 2 (ST2), 5299 nt, accession No DQ000496 [gi: 66356133].

Phylogenetic trees were constructed based on alignments of the isolates ST1 and ST2 and the viruses in the Parvovirinae subfamily. Results from full-length nucleotide sequences as well as nucleotide and deduced amino acid sequences of the two major open reading frames (ORFs) were consistent and confirmed that the isolates ST1 and ST2 group with MVC and BPV, as expected from the BLAST results. It has previously been recognized that MVC and BPV form a separate clade within the Parvovirinae, and the International Committee on Taxonomy of Viruses (ICTV) has recently assigned a separate genus with the name Bocavirus to BPV and MVC. The new virus is clearly separate from BPV and MVC, having only 43% amino acid identity to the nearest neighbor MVC in both major ORFs. The distance to BPV is remarkably similar: 42% amino acid identity in both major ORFs. We therefore conclude that the isolates ST1 and ST2 represent a previously unknown species of the genus Bocavirus.

The nucleotide sequence of HBoV genomic DNA of isolates ST1 and ST2 are shown in SEQ ID NO: 1 and SEQ ID NO: 2, respectively. The two HBoV isolates ST1 and ST2 are closely related, differing at only 26 nucleotide positions.

The genomic organization of HBoV closely resembles that of the other known bocaviruses BPV and MVC. Like in all members of the Parvovirinae subfamily, there are two major ORFs encoding a non structural protein (NS1) and at least 2 capsid proteins (VP1, VP2), respectively.

HBoV NS1 is encoded by nucleotides 183 to 2102 of SEQ ID NO: 1 and nucleotides 253 to 2172 of SEQ ID NO: 2, and has the amino acid sequence shown in SEQ ID NO: 3.

HBoV VP1 of ST1 is encoded by nucleotides 2986 to 5001 of SEQ ID NO: 1, and has the amino acid sequence shown in SEQ ID NO: 5.

HBoV VP1 of ST2 is encoded by nucleotides 3056 to 5071 of SEQ ID NO: 2, and has the amino acid sequence shown in SEQ ID NO: 7.

A second ORF within the ORF encoding VP1 begins at nucleotide position 3373 of SEQ ID NO: 1 and at nucleotide position 3443 of SEQ ID NO: 2. Nucleotides 3373 to 5001 of SEQ ID NO: 1 encode a second ST1 capsid protein VP2, which has the amino acid sequence shown in SEQ ID NO: 6. Nucleotides 3443 to 5071 of SEQ ID NO: 2 encode a second ST2 capsid protein VP2, which has the amino acid sequence shown in SEQ ID NO: 8.

Eighteen of the 26 nucleotide differences between the ST1 genomic DNA sequence SEQ ID NO: 1 and the ST2 genomic DNA sequence SEQ ID NO: 2, including the only three non-synonymous substitutions, occur in the capsid gene encoding VP1 and VP2 (FIG. 1B).

Like MVC and BPV, HBoV also has a third, middle ORF. In MVC and BPV this ORF encodes a non-structural protein with unknown function, named NP-1 [5, 6]. The mid ORF product NP-1 of HBoV is encoded by nucleotides 2340 to 2999 of SEQ ID NO: 1 and by nucleotides 2410 to 3069 of SEQ ID NO: 2, and has amino acid sequence SEQ ID NO: 4. HBoV NP-1 is homologous to MVC and BPV NP-1, having 47% amino acid identity to NP-1 of both MVC and BPV. This further supports the classification of HBoV as a Bocavirus.

HBoV polypeptides, including NS1, NP-1, VP1 and VP2 polypeptides as well as polypeptides with amino acid sequences at least 90, 95, 98 or 99% identity to the said NS1, NP-1, VP and VP2 polypeptides, form part of the invention, as do fragments e.g. peptide fragments of the polypeptides. Fragments are typically at least or about 10 amino acids in length, e.g. at least or about 15, 20, 25, 30, 35, 40, 50, 75, 100, 150 or 200 amino acids in length. For example, a fragment may be up to 200 amino acids in length, e.g. between 50 and 200 amino acids. Polypeptides comprising such fragments, and polypeptides and fragments that differ at one or more residues through substitution, addition or deletion, are also included in the invention.

HBoV nucleic acid molecules, nucleic acid molecules encoding polypeptides and fragments according to the invention, and nucleic acid molecules that specifically hybridise to nucleotide sequences disclosed herein are all aspects of the invention. The nucleic acid molecules may be provided as plasmids and vectors comprising the HBoV sequences (e.g. expression vectors, viral and non-viral vectors).

The nucleic acid and polypeptide sequences of HBoV constitute diagnostic keys to this virus. Nucleic acids and polypeptides of the virus described herein can be used as the basis for designing and/or producing diagnostic materials for determining whether an individual is or has been infected with HBoV, for example by testing for, identifying or demonstrating the presence of the virus in a sample, or by testing for the presence of anti-HBoV antibody in a sample.

Diagnostic assays can be performed to test for the presence of human bocavirus, or an antibody to human bocavirus, in a sample. Samples may be derived from individuals to be tested, especially babies or children, individuals with respiratory tract infections, blood donors and/or pregnant women. Samples may be taken from individuals suspected to be infected with parvovirus, especially bocavirus, and/or individuals with symptoms or conditions associated with parvoviral, especially bocavirus, infection, such as respiratory distress, wheezing, asthma, bronchitis, interstitial infiltrates (e.g. as indicated by chest X-ray) and/or fever. For diagnostic assays, a test sample may be provided in liquid form. A sample may be from the respiratory tract, e.g. a nasopharyngeal aspirate sample, or it may be e.g. a faecal or blood sample. Serological testing to determine the presence of anti-HBoV antibodies is normally done on blood samples.

In some embodiments of the invention, a sample is tested for HBoV by determining whether HBoV nucleic acid or polypeptide is present in the sample. Various methods are available to the skilled person for testing the sample, for example testing for hybridisation of HBoV nucleic acid to a specific primer or probe, or testing for binding of HBoV polypeptide to a specific binding member. Detection of the presence of HBoV nucleic acid or HBoV polypeptide in the sample indicates that the sample is positive for HBoV.

For example, the sample may be tested by being contacted with a specific binding member such as an antibody under appropriate conditions for specific binding. The binding member may optionally be labelled with a detectable label. Examples of suitable labels are described elsewhere herein. For example, the label may be a fluorescent label. Antibodies can be labelled with e.g. coloured latex, colloidal gold or colloidal selenium for detection by eye, or with an enzyme producing a detectable, e.g. coloured, product when a substrate is added. Binding may then be determined, e.g. using a reporter system. Where a panel of antibodies is used, different reporting labels may be employed for each antibody so that binding of each can be determined. Testing for binding of HBoV polypeptide to a specific binding member may employ e.g. immunofluorescence (IF), immunochromatography, or an enzyme immunoassay (EIA).

For example, a method of testing a sample for the presence of an HBoV polypeptide by determining binding to a binding member, e.g. antibody, may comprise:

(i) providing a test sample, e.g. on a support e.g. an inert solid support such as a glass slide;
(ii) contacting the test sample with binding members labelled with a detectable label e.g. a fluorescent label, under conditions in which the binding member binds to an HBoV polypeptide (if present) to form a binding member-polypeptide complex;
(iii) washing the sample or support to remove any unbound binding member; and
(iv) testing for the presence of the detectable label, wherein the presence of the detectable label indicates that the presence of HBoV polypeptide in the sample, i.e. that the sample is positive for human bocavirus.

Alternatively, a method of testing a sample for the presence of an HBoV polypeptide by determining binding to a binding member, e.g. antibody, may comprise:

(i) providing a test sample, e.g. on a support e.g. an inert solid support such as a glass slide;
(ii) contacting the test sample with a specific binding member against an HBoV polypeptide under conditions in which the binding member binds an HBoV polypeptide, if present, to form a binding member-polypeptide complex;
(iii) washing the sample to remove any unbound specific binding member;
(iv) contacting the sample with a second specific binding member, wherein the second specific binding member binds the said specific binding member against an HBoV polypeptide, if present, and wherein the second specific binding member is labelled with a detectable label, e.g. the second binding member may be a labelled anti-Ig antibody;

(v) washing the sample to remove any unbound specific binding member; and (iv) testing for the presence of the detectable label, wherein the presence of the detectable label indicates the presence of HBoV polypeptide in the sample.

A sample may be fixed to the support for example by allowing the sample to dry on to the support.

Where the label is a fluorescent label, methods may comprise testing for fluorescence, e.g. by fluorescence microscopy. Alternatively, detection of the label may be by eye, where the label is visually detectable e.g. coloured latex, colloidal gold or colloidal selenium. Detection by enzyme-linked assay is also possible, where the binding member is labelled with an enzyme that produces a detectable, e.g. coloured, product when a substrate is added.

A method using EIA normally comprises:
providing a binding member, e.g. an antibody, against HBoV on a support, wherein the binding member may be immobilised on the support, and wherein the support is typically an inert solid such as a polystyrene plate (e.g. microtitre plate), a nitrocellulose membrane or microparticles e.g. latex microparticles or paramagnetic beads;
contacting the binding member with the test sample under conditions in which the binding member binds to an HBoV polypeptide (if present) to form a binding member-polypeptide complex;
washing the complex to remove any unbound protein and/or other compounds from the sample;
contacting the complex with a second binding member, e.g. antibody, against HBoV, wherein the second binding member is linked to an enzyme that catalyses conversion of a substrate to a detectable product, thereby forming a binding member-polypeptide-binding member-enzyme complex if polypeptide is present;
washing away any unbound second binding member; and
contacting the enzyme with the substrate and assaying for the presence of the detectable product;
wherein detection of the detectable product indicates the presence of HBoV polypeptide in the sample.

Alternatively, immunochromatography-type methods may be used to test a sample for the presence of an HBoV polypeptide. A method may comprise providing a device comprising a body, e.g. an absorbent membrane, on which one or more binding members, e.g. antibodies, against HBoV are supported, wherein a test sample is passable through the body by capillary flow such that the sample contacts the one or more binding members. The device may comprise a detection area for detection of binding member-polypeptide complexes. The device may be designed such that HBoV polypeptide present in the sample can bind a said binding member to form a binding member-polypeptide complex, wherein the complex accumulates in a designated area of the body of the device where it may be detected. A method may comprise allowing a test sample to pass through the body of the device by capillary flow, and determining whether a binding member-polypeptide complex is present in the detection area, wherein presence of the complex in the detection area indicates that HBoV polypeptide is present in the sample.

The device also forms an aspect of the present invention. The device may be disposable, e.g. it may be a single-use test device.

The binding members supported on the body of the device may be labelled or unlabelled. Where the binding members are labelled, the complex may be detected in the detection area by detecting the label. Accordingly, a method may comprise determining whether the label is present in the detection area. Where the binding members are unlabelled, the complex may be detected in the detection area by contacting the complex with a second binding member, wherein the second binding member is labelled with a detectable label, and wherein the second binding member binds to the complex e.g. to the HBoV polypeptide or to the binding member against HBoV.

Detectable labels are described elsewhere herein. Detection of the label may be by eye, where the label is visually detectable e.g. coloured latex, colloidal gold or colloidal selenium. Detection by enzyme-linked assay is also possible, where the binding member is labelled with an enzyme that produces a detectable, e.g. coloured, product when a substrate is added. The label may be a fluorescent label, detectable by detecting fluorescence e.g. by fluorescence microscopy.

A specific binding member such as an antibody may be used to isolate and/or purify its binding partner polypeptide from a test sample, to allow for sequence and/or biochemical analysis of the polypeptide to determine whether it has the sequence and/or properties of the polypeptide of interest, or if it is a mutant or variant form. Amino acid sequencing is routine in the art using automated sequencing machines.

Probes and primers can be used to identify human bocaviral nucleic acid in a sample. A method may include hybridisation of one or more (e.g. two) probes or primers to target nucleic acid in the sample. A test sample may be probed under conditions for selective hybridisation and/or subjected to a specific nucleic acid amplification reaction such as the polymerase chain reaction (PCR). A method may include hybridisation of one or more (e.g. two) probes or primers to target nucleic acid. The hybridisation may be as part of a PCR procedure e.g. as described in more detail below, or as part of a probing procedure not involving PCR.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR or nucleic acid sequence based amplification (NASBA), ligase chain reaction (LCR), RNAase cleavage and allele specific oligonucleotide probing. Any of these methods, or any other suitable method, may be used to test a sample for the presence of HBoV nucleic acid.

NASBA is a method designed for amplification of RNA targets. An exponential amplification is achieved at stable 41° C. temperature by the activities of the enzymes AMV-RT, RNase H, and T7 DNA-dependent RNA polymerase. NASBA will amplify also DNA, in particular single stranded-DNA, and can be modified by the skilled person for use in the detection of HBoV DNA. Alternatively, NASBA can be used to identify replicating HBoV by identification of mRNA transcripts. NASBA is described in ref. [7].

LCR is an established method for molecular diagnostics and is an alternative to PCR. For LCR, the sample, or extracted DNA from the sample, is mixed with four oligonucleotide probes, which are complementary to a specific target region of HBoV, and thermostable ligase. The probes are designed to hybridize adjacently to each other on the target DNA, one pair to the sense strand, and the other pair to the antisense strand. In the presence of the template molecule they will be ligated to a longer molecule. By cycling the temperature this hybridization and ligation reaction will be repeated and the ligated product accumulated exponentially, and can be detected by a range of techniques, as for PCR.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells. Those skilled in the art can employ suitable conditions of the desired stringency for selective hybridisation, taking into account factors such as oligonucleotide length and base composition, temperature and so on.

The skilled person is readily able to design suitable probes, label them and devise suitable conditions for the hybridisation reactions, assisted by textbooks such as Sambrook et al (1989) and Ausubel et al (1992). Those skilled in the art can employ suitable conditions of the desired stringency for selective hybridisation, taking into account factors such as oligonucleotide length and base composition, temperature and so on. Hybridisation may be performed under highly stringent conditions, such as 6×SSC at a temperature of 65° C. For oligonucleotide primers, hybridisation may be performed under hybridising conditions for PCR, e.g. at 54° C.

Nucleic acid probes and oligonucleotide primers may be produced that specifically hybridise to human bocaviral nucleic acids including nucleic acid molecules comprising nucleotide sequences described herein. The bocavirus genome may be present as a plus- or minus-stranded single-stranded DNA molecule in virus particles or infected cells. The probe or primer may hybridise to a nucleic acid molecule with a nucleotide sequence described herein or to a nucleic acid molecule with a nucleotide sequence that is the complement of any of the sequences described herein. Assays may be for detecting detect mRNA or genomic DNA of bocavirus, where genomic DNA may comprise nucleotide sequences shown herein or the complement thereof. For example, oligonucleotide or polynucleotide fragments of SEQ ID NO: 1 or SEQ ID NO: 2 or the complementary sequence thereof can be used as primers or probes. Such primers and probe sequences may be modified by addition, substitution, insertion or deletion of one or more nucleotides, and the skilled person will be able to design suitable modified sequences that retain ability to hybridise with the target sequence.

PCR may be used to test for, identify or demonstrate the presence of human bocaviral nucleic acid in a sample. Such an assay may be used diagnostically to determine whether an individual is infected with HBoV. PCR involves use of a pair of primers, termed "forward" and "reverse" primers, which hybridise specifically to two complementary target nucleic acid strands, respectively. Thus, one primer may specifically hybridise to SEQ ID NO: 1 or SEQ ID NO: 2 and the second primer may specifically hybridise to the complement of SEQ ID NO: 1 or SEQ ID NO: 2.

PCR techniques for the amplification of nucleic acid are described in refs 8, 9, 10, 11 and 12. PCR comprises steps of denaturation of template nucleic acid (where necessary, for a double-stranded template), annealing of primers to target nucleic acid, and polymerisation of target nucleic acid to produce a specific DNA product corresponding to the nucleic acid located between (and including) the forward and reverse primers. The product is amplified through repetition of these steps. PCR can thus be used to amplify specific sequences from genomic DNA or specific RNA sequences.

HBoV has a single stranded DNA genome. PCR of HBoV nucleic acid involves (i) first primer hybridisation, in which one primer binds to HBoV nucleic acid, (ii) polymerisation from first primer to produce DNA strand complementary to initial HBoV nucleic acid strand, (iii) denaturation to separate complementary strands and primers, (iv) hybridisation of first and second primer to complementary target nucleic acid strands, whereby second primer hybridises to complementary strand synthesised from first primer, (v) polymerisation from first and second primer, (vi) repetition of steps (iii)-(v) for a suitable number of cycles.

Primers may hybridise specifically to HBoV nucleic acid encoding NP-1, e.g. to a sequence of nucleotides 2340 to 2999 shown in SEQ ID NO: 1 and nucleotides 2410 to 3069 shown in SEQ ID NO: 2. Example primer sequences hybridise to the N-terminal region of NP-1, e.g. the primers shown in SEQ ID NO: 9 and SEQ ID NO: 10.

The skilled person can select a suitable length nucleic acid to use as a PCR primer. For example, an oligonucleotide primer may be at least 10, 12 or 15 nucleotides in length. Preferably an oligonucleotide primer has a length of 30, 27 or 24 nucleotides or less. For example, it may be about 12, 15, 18, 21 or 24 nucleotides in length.

Preferably, the forward and reverse primers hybridise within a distance of 500 nucleotides from each other, and thereby define a region of 500 nucleotides or less for amplification by PCR. Thus, the specific nucleotide sequence to which the forward primer hybridises is within 500 nucleotides of the specific nucleotide sequence to which the reverse primer hybridises on the complementary strand.

An assay may detect human bocavirus nucleic acid, e.g. nucleic acid comprising a nucleotide sequence as shown herein, using one or more nucleic acid probes or primers that hybridise specifically to human bocavirus nucleic acid.

In a preferred embodiment, an assay method comprises providing a test sample, and testing for the presence of human bocavirus nucleic acid in the sample using PCR with oligonucleotide primers that hybridise specifically to human bocavirus nucleotide sequences. The assay may comprise adding oligonucleotide PCR primers to the sample, placing the sample in conditions for PCR, and then testing the sample for the presence of a PCR product. Conditions for PCR preferably include at least 20, 25, 30 or 35 PCR cycles. Detection of PCR product, e.g. by visualisation of a band of the expected size following gel electrophoresis of the sample, indicates that the sample is positive for human bocavirus nucleic acid. As an additional check, the PCR-product may be sequenced in order to confirm that it is bocaviral nucleic acid. Absence of a PCR product indicates that the sample is negative for human bocavirus nucleic acid.

Preferably, the assay is capable of detecting multiple isolates of HBoV, and primers directed to the NP-1 ORF of human bocaviral nucleic acid may thus be preferred.

Example 1 below describes in detail the performance of PCR assay methods according to an embodiment of the invention.

Methods of the invention may comprise detecting the presence of HBoV polypeptide or nucleic acid in a sample and thus concluding that the sample is positive for human bocavirus, indicating that the individual from whom the sample was obtained is infected with bocavirus.

Further aspects of the invention are kits for testing a sample for the presence of human bocavirus, e.g. testing for HBoV nucleic acid or HBoV polypeptide in a sample. For example, a kit for testing a sample for an HBoV polypeptide may be for use in a method of determining whether a polypeptide in a sample binds to a specific binding member, as described above.

A kit may comprise specific binding members for one or more HBoV polypeptides e.g. antibody molecules, which may be labelled with a detectable label, or may be unlabelled. Examples of suitable detectable labels are described elsewhere herein. The specific binding members may be provided in solution, e.g. packaged in a container e.g. a phial. A kit may comprise unlabelled specific binding members, e.g. antibodies, for an HBoV polypeptide, and labelled specific binding members that bind the unlabelled specific binding members, e.g. anti Ig antibodies. Labelled and unlabelled binding members may be provided in separate containers e.g. phials. Where the label is an enzyme that catalyses conversion of a substrate to a detectable product, a kit may further comprise a suitable enzyme substrate for detection of the label. For example, the kit may comprise a container e.g. a bottle or phial comprising substrate for the enzyme, typically a solution, which may be provided at a suitable concentration for use in EIA.

A kit may comprise a device for testing a sample for human bocavirus, the device comprising a body on which one or more specific binding members for an HBoV polypeptide are supported, wherein a test sample is passable through the body by capillary flow such that the sample contacts the one or more binding members to form a binding-member polypeptide complex if HBoV polypeptide is present in the sample, and wherein the body also comprises a detection area for detection of the binding member-polypeptide complexes. The binding members may be labelled or unlabelled. The device may be a single-use test device for an immunochromatography assay, on which a sample is to be provided, and containing e.g. labelled or unlabelled specific binding members for HBoV polypeptides. The kit may further comprise phials of diluents, and/or labelled or unlabelled specific binding members for HBoV polypeptides e.g. antibody molecules, e.g. provided in solution, as described above.

A kit may comprise specific binding members for one or more HBoV polypeptides, wherein the binding members are immobilised on a support. The support is preferably an inert solid such as a polystyrene plate (e.g. microtitre plate), a nitrocellulose membrane or microparticles e.g. latex microparticles or paramagnetic beads. Normally the binding members bound to the support are unlabelled.

Washing solution or solutions, for washing away unbound protein, other compounds from the sample, or unbound binding member, may also be included in kits, normally in one or more containers e.g. bottles or phials. Normally the elements of a kit e.g. support; labelled binding member; unlabelled binding member; substrate and/or washing solution are separately contained in the kit e.g. provided in separate packages or containers from one another. A kit may also include one or more articles and/or reagents for performance of the method, such as means for providing the test sample itself, e.g. a swab for removing cells from the buccal cavity or a syringe for removing a blood sample (such components generally being sterile). A kit may further comprise a support, e.g. an inert solid support such as a glass slide, on which a sample is to be provided. As will be apparent to the skilled person, components included in the kit will depend on the nature of the method for which it is intended.

Nucleic acid primers may be provided as part of a kit, e.g. in a suitable container. The primers are typically provided in separate containers within a kit package, and are normally in the form of sterile solutions. The kit may include instructions for use of the nucleic acid, e.g. in PCR and/or a method for determining the presence of nucleic acid of interest in a test sample. A kit wherein the nucleic acid is intended for use in PCR may include one or more other reagents required for the reaction, such as polymerase, nucleosides, buffer solution etc. The nucleic acid may be labelled. A kit for use in determining the presence or absence of nucleic acid of interest may include one or more articles and/or reagents for performance of the method, such as means for providing the test sample itself, e.g. a swab for removing cells from the buccal cavity or a syringe for removing a blood sample (such components generally being sterile).

HBoV polypeptides can also be used to investigate whether an individual has antibodies for HBoV. The presence of antibodies for HBoV indicates that the individual is or has been infected with HBoV. Accordingly, an aspect of the invention relates to testing of a sample for the presence of antibody to one or more HBoV polypeptides, preferably antibody for VP1 and/or VP2, by determining whether antibodies in the sample bind to one or more HBoV polypeptides. Normally, the sample is a blood sample. The method typically comprises providing an HBoV polypeptide on a support. Normally the polypeptide is immobilised on the support. The support is typically an inert solid such as a polystyrene plate (e.g. microtitre plate), a nitrocellulose membrane or microparticles e.g. latex microparticles or paramagnetic beads. The method generally further comprises contacting the HBoV polypeptide with the test sample under conditions in which the HBoV polypeptide binds to an antibody for HBoV (if present) to form a polypeptide-antibody complex; and determining or testing for formation of a polypeptide-antibody complex. Normally, the support is washed after contacting the HBoV polypeptide with the sample, to remove any unbound protein and/or other compounds from the sample.

Determining or testing for formation of the complex may comprise contacting the complex with a detectably-labelled antibody, which may be specific for immunoglobulin, e.g. directed against the Fc domain of IgG. Any unbound anti-Ig antibody is then normally washed away, before assaying for the presence of the detectably-labelled antibody bound to the complex. Detection of the labelled antibody indicates the presence of antibody against HBoV polypeptide in the sample.

Normally, an enzyme immunoassay EIA is used to detect the labelled antibody. Thus, the anti-Ig antibody may be linked to an enzyme that catalyses conversion of a substrate to a detectable product. There is a range of detection systems for EIA and other immunoassays available to the skilled person, such as alkaline phosphatase, peroxidase and chemoilluminescent assays. Assaying for the presence of the labelled antibody may comprise contacting the enzyme with the substrate and assaying for the presence of the detectable product. The product can be detected by eye or in an instrument designed for the purpose, for example a spectrophotometer designed for microtitre plates or a large multipurpose clinical laboratory assay instrument.

For analysis of human samples, the anti-Ig antibody is normally specific for the Fc region of human immunoglobulins, e.g human IgG or IgM.

Materials for detecting anti-HBoV antibody in a sample may be provided in kit form. Preferably the kit is for use in a method comprising EIA, e.g. as described above. A kit may comprise an HBoV polypeptide e.g. HBoV VP1 or VP2, or more than one HBoV polypeptide, bound to a support. Normally the polypeptide is immobilised on the support. The support is preferably an inert solid such as a polystyrene plate (e.g. microtitre plate), a nitrocellulose membrane or microparticles e.g. latex microparticles or paramagnetic beads. The kit may also comprise antibody specific for immunoglobulin, e.g. the Fc domain of anti-IgG, wherein the anti-Ig antibody is detectably labelled. For example it may be linked to an enzyme that catalyses conversion of a substrate to a detectable product. The kit may comprise a container e.g. a bottle or phial comprising substrate for the enzyme, typically a solution, and preferably at a suitable concentration for use in EIA, e.g. ELISA. Washing solution or solutions, for washing away unbound protein, other compounds from the sample, or unbound anti-Ig antibody, may also be included in the kit, normally in one or more containers e.g. bottles or phials. Normally the elements of the kit e.g. polypeptide on support; anti-Ig antibody; substrate and/or washing solution are separately contained in the kit e.g. provided in separate packages or containers from one another.

Specific binding members for HBoV can be produced by the skilled person. A specific binding member for HBoV binds specifically to an epitope on HBoV, typically to an HBoV polypeptide. For example, a specific binding-member may be an antibody molecule or a non-antibody protein that comprises an antigen-binding site. The term "specific" as used herein generally refers to the situation in which a specific binding member does not show any significant binding to molecules other than its specific binding partner(s). The term is also applicable where e.g. an antigen-binding site is specific for a particular epitope that is carried by a number of antigens, in which case the specific binding member carrying the antigen-binding site will be able to bind to the various antigens carrying the epitope.

Preferably, the specific binding member is for an HBoV polypeptide encoded by a nucleic acid molecule shown herein, such as NS1, NP-1, VP1 or VP2. Preferably, the specific binding molecule is for HBoV capsid protein e.g. VP1 and/or VP2.

Typically, the specific binding member is an antibody molecule. The term "antibody" describes an immunoglobulin whether natural or partly or wholly synthetically produced. The term also covers any polypeptide or protein comprising an antibody antigen-binding site. The term "antigen-binding site" describes the part of a molecule that binds to and is complementary to all or part of the target antigen. In an antibody molecule it is referred to as the antibody antigen-binding site, and comprises the part of the antibody that specifically binds to and is complementary to all or part of the target antigen. Where an antigen is large, an antibody may only bind to a particular part of the antigen, which part is termed an epitope. An antibody antigen-binding site may be provided by one or more antibody variable domains. Preferably, an antibody antigen-binding site comprises an antibody light chain variable region (VL) and an antibody heavy chain variable region (VH). Antibody molecules and fragments that comprise an antibody antigen-binding site include Fab, scfv, Fv, dAb, Fd, minibodies and diabodies. As antibodies can be modified in a number of ways, the term "antibody molecule" should be construed as covering any specific binding member or substance having an antibody antigen-binding site with the required specificity. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide are therefore included. Cloning and expression of chimeric antibodies are described in EP-A-0120694 and EP-A-0125023, and a large body of subsequent literature.

For therapeutic use the specific binding member is preferably a human or humanized antibody molecule. Various techniques for generating human or humanized antibodies are available [13, 14, 15]. Binding members for diagnostic use are normally monoclonal or polyclonal antibodies derived from laboratory animals.

Alternatively, an antigen binding site may be provided by means of arrangement of complementarity determining regions (CDRs) on non-antibody protein scaffolds such as fibronectin or cytochrome B, or by randomising or mutating amino acid residues of a loop within a protein scaffold to confer binding specificity for a desired target [16, 17]. The scaffold may be a human or non-human protein.

A specific binding member of the invention may carry a detectable label, such as an enzyme that catalyses a reaction producing a detectable product, e.g. for use in EIA. Other detectable labels include for example fluorescent labels, radiolabels, biotin, coloured latex, colloidal gold or colloidal selenium.

Compounds that bind to HBoV polypeptides, including specific binding members for HBoV polypeptides, and inhibitors of HBoV polypeptides, may be identified by screening candidate agents e.g. from compound libraries. For example, a method of identifying a compound that binds an HBoV polypeptide may comprise exposing an HBoV polypeptide or a fragment thereof to a test agent, and determining whether the test agent binds to the HBoV polypeptide or fragment thereof. Preferably the HBoV polypeptide is VP1 or VP2 or an extracellular domain or fragment of VP1 or VP2. The method may further comprise determining whether the test agent inhibits the function of the HBoV polypeptide, for example whether the agent inhibits the ability of HBoV to infect a cell e.g. in an in vitro assay. Compounds that bind HBoV polypeptide, including specific binding members and inhibitors, may be useful as antiviral therapeutics for treating or preventing HBoV infection. Such a compound may be formulated into a composition comprising a pharmaceutically acceptable excipient.

An HBoV nucleic acid, polypeptide or fragment according to the invention may be used for raising an immune response in an individual, for example for generating antibodies against HBoV polypeptides. Alternatively, HBoV particles, or purified fragments thereof, may be used for raising an immune response in an individual, for example for generating antibodies against HBoV polypeptides. For example live e.g. live attenuated, or killed, e.g. formalin inactivated, HBoV may be used. HBoV particles may be composed of a single copy of the HBoV genome as a single-stranded DNA, surrounded by the virus capsid. The capsid may comprise VP1 and VP2, of which VP2 may be the main component.

An HBoV particle or purified fragment thereof and/or an HBoV nucleic acid molecule, polypeptide or fragment thereof may be formulated into a composition comprising a pharmaceutical excipient, e.g. formulated for administration by injection. Adjuvant may also be included in the composition. The nucleic acid may be packaged e.g. in a liposome or may be free in solution. HBoV nucleic acid molecules, polypeptides or fragments thereof for may be provided by, contained as part of, or isolated from HBoV particles e.g. attenuated or killed HBoV e.g. formalin inactivated HBoV, or may be recombinantly produced. For example, VP1 and/or VP2 may be expressed in a recombinant system to produce and virus-like particles (VLPs), and VLPs may be formulated into a composition comprising a pharmaceutical excipient, e.g. formulated for administration by injection. The compositions may be used for inducing an immune response, for example for raising antibodies and/or for vaccination of individuals against HBoV.

Specific binding members, polypeptides, nucleic acid molecules and fragments according to the invention are normally provided in isolated form. The term "isolated" means that they are normally free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. They may be formulated with diluents or adjuvants and still for practical purposes be isolated—for example specific binding members will normally be mixed carriers if used to coat microtitre plates for use in immunoassays, or will be mixed with pharmaceutically acceptable carriers or diluents when used in diagnosis or therapy. Specific binding members may be glycosylated or unglycosylated.

The following non-limiting examples are for purposes of illustration only.

EXAMPLES

Example 1

Diagnostic PCR for Human Bocavirus

Experiments were performed in a diagnostic laboratory setting, ensuring that necessary precautions to avoid contamination were taken. Samples were screened in pools of ten, and for PCR-positive pools, samples were extracted and amplified individually. Positive and negative controls were included in each experiment. DNA was extracted by QIAamp DNA Blood Mini Kit (Qiagen). Five µl extracted DNA was used as template for the PCR reaction. The 50 µl reaction mix consisted of 1× GeneAmp PCR buffer II (Applied Biosystems) (100 mM Tris-HCl pH 8.3, 500 mM KCl), 2.5 mM $MgCl_2$, 0.2 mM each dNTP, 20 pmol each of the primers 188F(GAGCTCTGTAAGTACTATTAC—SEQ ID NO: 9) and 542R (CTCTGTGTTGACTGAATACAG—SEQ ID NO: 10), and 2.5 U of AmpliTaq Gold DNA polymerase (Applied Biosystems). After 10 min at 94° C., 35 cycles of amplification (94° C. 1 min, 54° C. 1 min, 72° C. 2 min) were performed. Products were visualized on an agarose gel. The expected product size was 354 bp. All PCR-products were sequenced in order to confirm that they were specific for HBoV.

Example 2

Incidence and Symptoms of Human Bocavirus Infection

In order to estimate the prevalence of HBoV in respiratory tract samples and the clinical picture associated with HBoV-infection, a series of PCR screening experiments was performed. As a first overview, 378 culture-negative nasopharyngeal aspirate samples drawn from November 2003 through September 2004 were screened for HBoV by a PCR assay targeting 354 base pairs in the NP-1 gene. These samples came from various clinics served by the Karolinska University Laboratory. 266 samples were from pediatric patients and 112 from adult patients. Seven samples were positive for HBoV DNA and all seven came from infants and children.

Therefore, a more detailed retrospective study was performed in the pediatric infectious diseases ward at the Karolinska University Hospital. All 540 available nasopharyngeal aspirates drawn in the ward (hospitalized patients only) from November 2003 through October 2004 were investigated, including some of the samples included in the first screening. Samples from 17 different patients (3.1%) were positive. The HBoV specificity of the PCR products was confirmed by sequencing. Fourteen HBoV-positive samples were negative for other viruses investigated (by IF and virus culture), while HBoV was detected along with another virus in 3 cases (two RSV, one adenovirus). Morbidity from LRTI is highest in the winter season, and this was reflected by sampling frequency as well as findings of HBoV (Table 1).

The medical records of the 14 patients infected with HBoV only were reviewed. All 14 children were admitted from home with respiratory distress of 1-4 days duration. Seven children had a history of wheezing bronchitis/asthma and were under daily treatment with inhaled beta-2-stimulans and steroids. Four of them had previously been hospitalized for wheezing bronchitis. Two children had chronic lung disease that originated in the neonatal period, and five patients had no history of previous respiratory tract problems. All patients had variable degree of respiratory distress, and fever was prevalent. Chest x-ray demonstrated interstitial bilateral infiltrates in 6 of 7 cases. Gastrointestinal symptoms, conjunctivitis or rash was not recorded in any case.

In order to establish that HBoV was the likely etiologic agent of the observed symptoms, and not just a coincidental finding, we investigated how findings of HBoV correlated to findings of other likely etiologic agents. In the 540 samples analyzed, a known viral pathogen (mainly influenza A virus or RSV) was identified by standard diagnostics (IF and virus culture) in 258 of the 540 patients (48%), and no virus was found by standard diagnostics in 282 patients (52%). 14 of the 17 HBoV findings were in the latter group. Thus, HBoV was primarily found in samples negative for other viruses ($p<0.01$, Fisher's exact test), providing an indication that it is an etiologic agent of LRTI in our patients.

Table 1

Findings of HBoV in nasopharyngeal aspirate samples drawn in the pediatric infectious diseases unit November 2003-October 2004 distributed per month.

| Month | Tested | Positive |
|---|---|---|
| Nov | 28 | 0 |
| Dec | 125 | 4 |
| Jan | 100 | 5 |
| Feb | 110 | 4 |
| Mar | 85 | 1 |
| Apr | 43 | 2 |
| May | 12 | 0 |
| Jun | 4 | 1 |
| Jul | 11 | 0 |
| Aug | 3 | 0 |
| Sep | 12 | 0 |
| Oct | 7 | 0 |
| Total | 540 | 17 |

Sequences

```
SEQ ID NO: 1 HBoV ST1 genomic DNA
   1 caaggaggag tggttatatg atgtaatcca taaccactcc caggaaatga cgtatgatag 61 ccaatcagaa ttgagtattg aacctatata agctgctgca cttcctgatt caatcagact 121 gcatccggtc tccggcgagt gaacatctct ggaaaaagct ccacgcttgt ggtgagtcta 181 ctatggcttt caatcctcct gtgattagag cttttctca acctgctttt acttatgtct
```

```
241   tcaaatttcc atatccacaa tggaaagaaa aagaatggct gcttcatgca cttttagctc
301   atggaactga acaatctatg atacaattaa gaaactcgcg tcctcatccg gatgaagaca
361   taatccgtga tgacttgctt atttctttag aagatcgcca ttttggggct gttctctgca
421   aggctgttta catggcaaca actactctca tgtcacacaa acaaaggaat atgtttcctc
481   gttgtgacat catagttcag tctgagctag gagagaaaaa cttacactgc catattatag
541   ttgggggaga aggactaagc aagaggaatg ctaaatcatc ctgtgctcag ttctatggtt
601   taatactagc tgaaataatt caacgctgca aatctcttct ggctacacgt ccttttgaac
661   ctgaagaggc tgacatattt cacacttaa aaaaggctga gcgagaggca tggggtggag
721   ttactggcgg caacatgcaa atccttcaat atagagatcg cagaggagac cttcatgcac
781   aaacagtgga tcctcttcgc ttcttcaaaa actacctttt acctaaaaat agatgtattt
841   catcttacag caaacctgat gtttgtactt ctcctgacaa ctggttcatt ttagctgaaa
901   aaacttactc tcacactctt attaacgggc tgccgcttcc agaacattac agaaaaaact
961   accacgcaac cctagataac gaagtcattc cagggcctca acaatggcc tatggaggac
1021  gtggtccgtg ggaacatctt cctgaggtag gagatcagcg cctagctgcg tcttctgtta
1081  gcactactta taaacctaac aaaaaagaaa aacttatgct aaacttgcta gacaaatgta
1141  aagagctaaa tctattagtt tatgaagact tagtagctaa ttgtcctgaa ctactcctta
1201  tgcttgaagg tcaaccagga ggggcacgcc ttatagaaca agtcttgggc atgcaccata
1261  ttaatgtttg ttctaacttt acagctctca catatctttt tcatctacat cctgttactt
1321  cgcttgactc agacaataaa gctttacagc ttttgttgat tcaaggctat aatcctctag
1381  ccgttggtca cgccctgtgc tgtgtcctga caaacaatt cgggaaacaa acactgtttt
1441  gcttttacgg gcctgcctca acaggtaaaa caaatatggc caaggcaatc gtccaaggga
1501  ttagacttta tgggtgtgtt aatcatttga acaaaggatt tgtatttaat gactgcagac
1561  aacgcttagt tgtttggtgg gaggagtgct taatgcacca ggattgggtg aacctgcaa
1621  agtgtatctt gggcgggaca gaatgcagaa ttgacgtcaa gcatagagac agtgtacttt
1681  taactcaaac acctgtaatt atatccacta accacgatat ctacgcggtt gttggtggca
1741  attctgtttc tcatgttcac gcggctccat taaaagaaag agtgattcag ctaaatttta
1801  tgaaacaact tcctcaaaca tttggagaaa tcactgctac tgagattgca gctcttctac
1861  agtggtgttt caatgagtac gactgtactc tgacaggatt taaacaaaaa tggaatttag
1921  ataaaattcc aaactcattt cctcttgggg tccttttgtcc tactcattca caggacttta
1981  cacttcacga aaacggatac tgcactgatt gcggtggtta ccttcctcat agtgctgaca
2041  attctatgta cactgatcgc gcaagcgaaa ctagcacagg agacatcaca ccaagtaagt
2101  aaatacgcat gcgcaagtaa ttcttttact ttcacttcgc tattttacc aattttact
2161  tttaggtgac ttgggggatt cggacggaga agacaccgag cctgagacat cgcaagtgga
2221  ctattgtcca cccaagaaac gtcgtctaac tgctccagca agtcctccaa actcacctgc
2281  gagctctgta agtactatta ctttctttaa cacttggcac cacagccac gtgacgaaga
2341  tgagctcagg gaatatgaaa acaagcatc gctcctacaa aagaaaggg agtccagaaa
2401  gaggggagag gaagagacac tggcagacaa ctcatcacag gagcaggagc cgcagcccga
2461  tccgacacag tggggagaga ggctcgggct catatcatca ggaacaccca atcagccacc
2521  tatcgtcttg cactgcttcg aagacctcag accaagtgat gaagacgagg gagagtacat
2581  cggggaaaaa agacaataga acaaatccat acactgtatt cagtcaacac agagcttcca
2641  atcctgaagc tccagggtgg tgtgggttct actggcactc tactcgcatt gctagagatg
```

-continued

```
2701  gtactaattc aatctttaat gaaatgaaac aacagtttca acagctacaa attgataata
2761  aaataggatg ggataacact agagaactat tgtttaatca aagaaaaca ctagatcaaa
2821  aatacagaaa tatgttctgg cactttagaa ataactctga ttgtgaaaga tgtaattact
2881  gggatgatgt gtaccgtagg cacttagcta atgtttcctc acagacagaa gcagacgaga
2941  taactgacga ggaaatgctt tctgctgctg aaagcatgga agcagatgcc tccaattaag
3001  agacagccta gagggtgggt gctgcctgga tacagatatc ttgggccatt taatccactt
3061  gataacggtg aacctgtaaa taacgctgat cgcgctgctc aattacatga tcacgcctac
3121  tctgaactaa taaagagtgg taaaaatcca tacctgtatt tcaataaagc tgatgaaaaa
3181  ttcattgatg atctaaaaga cgattggtca attggtggaa ttattggatc cagttttttt
3241  aaaataaagc gcgccgtggc tcctgctctg ggaaataaag agagagccca aaaagacac
3301  ttttactttg ctaactcaaa taaaggtgca aaaaaaacaa aaaaagtga acctaaacca
3361  ggaacctcaa aaatgtctga cactgacatt caagaccaac aacctgatac tgtggacgca
3421  ccacagaacg cctcagggg aggaacagga agtattggag gaggaaaagg atctggtgtg
3481  gggatttcca ctggaggtg ggtcggaggt tctcacttt cagacaaata tgtggttact
3541  aaaaacacaa gacaatttat aaccacaatt cagaatggtc acctctacaa aacagaggcc
3601  attgaaacaa caaaccaaag tggaaaatca cagcgctgcg tcacaactcc atggacatac
3661  tttaacttta atcaatacag ctgtcacttc tcaccacaag attggcagcg ccttacaaat
3721  gaatataagc gcttcagacc taaagcaatg caagtaaaga tttacaactt gcaaataaaa
3781  caaatacttt caaatggtgc tgacacaaca tacaacaatg acctcacagc tggcgttcac
3841  atcttttgtg atggagagca tgcttaccca aatgcatctc atccatggga tgaggacgtc
3901  atgcctgatc ttccatacaa gacctggaaa cttttcaat atggatatat tcctattgaa
3961  aatgaactag cagatcttga tggaaatgca gctggaggca atgctacaga aaaagcactt
4021  ctgtatcaga tgcctttttt tctacttgaa aacagtgacc accaagtact tagaactggt
4081  gagagcactg aatttacttt taactttgac tgtgaatggg ttaataatga aagagcatac
4141  attcctcctg gattgatgtt caatccaaaa gttccaacaa gaagagttca gtacataaga
4201  caaaacggaa gcacagcagc cagcacaggc agaattcagc catactcaaa accaacaagc
4261  tggatgacag gacctggcct gctcagtgca cagagagtag gaccacagtc atcagacact
4321  gctccattca tggtttgcac taacccagaa ggaacacaca taaacacagg tgctgcagga
4381  tttggatctg gctttgatcc tccaagcgga tgtctggcac caactaacct agaatacaaa
4441  cttcagtggt accagacacc agaaggaaca ggaaataatg gaaacataat tgcaaaccca
4501  tcactctcaa tgcttagaga ccaactccta tacaaaggaa accagaccac atacaatcta
4561  gtgggggaca tatggatgtt tccaaatcaa gtctgggaca gatttcctat caccagagaa
4621  aatccaatct ggtgcaaaaa accaagggct gacaaacaca caatcatgga tccatttgat
4681  ggatccattg caatggatca tcctccaggc actatttta taaaaatggc aaaaattcca
4741  gtaccaactg caacaaatgc agactcatat ctaaacatat actgtactgg acaagtcagc
4801  tgtgaaattg tatgggaagt agaaagatac gcaacaaaga actggcgtcc agaaagaaga
4861  catactgcac tcgggatgtc actgggagga gagagcaact acacgcctac ataccacgtg
4921  gatccaacag gagcatacat ccagcccacg tcatatgatc agtgtatgcc agtaaaaaca
4981  aacatcaata agtgttgta atcttataag cctcttttt gcttctgctt acaagttcct
5041  cctcaatgga caagcggaaa gtgaagggtg actgtagtcc tgagctcatg ggttcaagac
```

-continued

```
5101 cacagcccga tggtagtggt gttaccgtct cgaacctagc cgacagccct tgtacattgt 5161 gggggagct gttttgtttg cttatgcaat cgcgaaactc tatatctttt aatgtgt
```

SEQ ID NO: 2 HBoV ST2 genomic DNA
```
   1 gccggcagac atattggatt ccaagatggc gtctgtacaa ccacgtcaca tataaaataa 61 taaatattca caaggaggag tggttatatg atgtaatcca taaccactcc caggaaatga 121 cgtatgatag ccaatcagaa ttgagtatta aacctatata agctgctgca cttcctgatt 181 caatcagact gcatccggtc tccggcgagt gaacatctct ggaaaaagct ccacgcttgt 241 ggtgagtcta ctatggcttt caatcctcct gtgattagag cttttctca acctgctttt 301 acttatgtct tcaaatttcc atatccacaa tggaaagaaa agaatggct gcttcatgca 361 cttttagctc atggaactga acaatctatg atacaattaa gaaactgcgc tcctcatccg 421 gatgaagaca taatccgtga tgacttgctt atttctttag aagatcgcca ttttgggct 481 gttctctgca aggctgttta catggcaaca actactctca tgtcacacaa acaaaggaat 541 atgtttcctc gttgtgacat catagttcag tctgagctag agagaaaaa cttacactgc 601 catattatag ttgggggaga aggactaagc aagaggaatg ctaaatcatc ctgtgctcag 661 ttctatggtt taatactagc tgagataatt caacgctgca atctcttct ggctacacgt 721 cctttgaac ctgaggaggc tgacatattt cacactctaa aaaggctga gcgagaggca 781 tggggtggag ttactggcgg caacatgcag atccttcaat atagagatcg cagaggagac 841 cttcatgcac aaacagtgga tcctcttcgc ttcttcaaaa actacctttt acctaaaaat 901 agatgtattt catcttacag caaacctgat gtttgtactt ctcctgacaa ctggttcatt 961 ttagctgaaa aaacttactc tcacactctt attaacgggc tgccgcttcc agaacattac 1021 agaaaaaact accacgcaac cctagataac gaagtcattc cagggcctca acaatggcc 1081 tatggaggac gtggtccgtg gaacatctt cctgaggtag gagatcagcg cctagctgcg 1141 tcttctgtta gcactactta taaacctaac aaaaaagaaa aactatgct aaacttgcta 1201 gacaaatgta aagagctaaa tctattagtt tatgaagact tagtagctaa ttgtcctgaa 1261 ctactcctta tgcttgaagg tcaaccagga ggggcacgcc ttatagaaca agtcttgggc 1321 atgcaccata ttaatgtttg ttctaacttt acagctctca catatctttt tcatctacat 1381 cctgttactt cgcttgactc agacaataaa gctttacagc ttttgttgat tcaaggctat 1441 aatcctctag ccgttggtca cgccctgtgc tgtgtcctga acaaacaatt cgggaaacaa 1501 aacactgttt gcttttacgg gcctgcctca acaggtaaaa caaatatggc caaggcaatc 1561 gtccaaggga ttagacttta tgggtgtgtt aatcatttga caaaggatt tgtatttaat 1621 gactgcagac aacgcctagt tgtttggtgg gaggagtgct taatgcacca ggattgggtg 1681 gaacctgcaa agtgtatctt gggcgggaca gaatgcagaa ttgacgtcaa gcatagagac 1741 agtgtacttt taactcaaac acctgtaatt atatccacta accacgtat ctacgcggtt 1801 gttggtggca attctgtttc tcatgttcac gcggctccat taaaagaaag agtgattcag 1861 ctaaattta tgaaacaact tcctcaaaca tttggagaaa tcactgctac tgagattgca 1921 gctcttctac agtggtgttt caatgagtac gactgtactc tgacaggatt taaacaaaaa 1981 tggaatttag ataaaattcc aaactcattt cctcttgggg tcctttgtcc tactcattca 2041 caggacttta cacttcacga aaacggatac tgcactgatt gcggtggtta ccttcctcat 2101 agtgctgaca attctatgta cactgatcgc gcaagcgaaa ctagcacagg agacatcaca 2161 ccaagtaagt aaatacgcat gcgcaagtaa ttcttttact ttcacttcgc tatttttacc
```

-continued

```
2221  aatttttact  tttaggtgac  ttgggggatt  cggacggaga  agacaccgag  cctgagacat
2281  cgcaagtgga  ctattgtcca  cccaagaaac  gtcgtctaac  tgctccagca  agtcctccaa
2341  actcacctgc  gagctctgta  agtactatta  ctttctttaa  cacttggcac  gcacagccac
2401  gtgacgaaga  tgagctcagg  gaatatgaaa  gacaagcatc  gctcctacaa  aagaaaaggg
2461  agtccagaaa  gaggggagag  gaagagacac  tggcagacaa  ctcatcacag  gagcaggagc
2521  cgcagcccga  tccgacacag  tggggagaga  ggctcgggct  catatcatca  ggaacaccca
2581  atcagccacc  tatcgtcttg  cactgcttcg  aagacctcag  accaagtgat  gaagacgagg
2641  gagagtacat  cggggaaaaa  agacaataga  acaaatccat  acactgtatt  cagtcaacac
2701  agagcttcca  atcctgaagc  tccagggtgg  tgtgggttct  actggcactc  tactcgcatt
2761  gctagagatg  gtactaattc  aatctttaat  gaaatgaaac  aacagtttca  acaactacaa
2821  attgataata  aaataggatg  ggataacact  agagaactat  tgtttaatca  aaagaaaaca
2881  ctagatcaaa  aatacagaaa  tatgttctgg  cactttagaa  ataactctga  ttgtgaaaga
2941  tgtaattact  gggatgatgt  gtaccgtaga  cacttagcta  atgtttcctc  acagacagaa
3001  gcagacgaga  taactgacga  ggaaatgctt  tctgctgctg  aaagcatgga  agcagatgcc
3061  tccaattaag  agacagccta  gagggtgggt  gctgcctgga  tacagatatc  ttgggccatt
3121  taatccactt  gataacggtg  aacctgtaaa  taacgctgat  cgcgctgctc  aattacatga
3181  tcacgcctac  tctgaactaa  taaagagtgg  taaaaatcca  tacctgtatt  tcaataaagc
3241  tgatgaaaaa  ttcattgatg  atctaaaaga  cgattggtca  attggtggaa  ttattggatc
3301  cagtttttt  aaaataaagc  gcgccgtggc  tcctgctctg  ggaaataaag  agagagccca
3361  aaaaagacac  ttttactttg  ctaactcaaa  taaaggtgca  aaaaaaacaa  aaaaaagtga
3421  acctaaacca  ggaacctcaa  aaatgtctga  cactgacatt  caagaccaac  aacctgatac
3481  tgtggacgca  ccacaaaaca  cctcaggggg  aggaacagga  agtattggag  gaggaaaagg
3541  atctggtgtg  gggatttcca  ctggagggtg  ggtcggaggt  tctcactttt  cagacaaata
3601  tgtggttact  aaaaacacaa  gacaatttat  aaccacaatt  cagaatggtc  acctctacaa
3661  aacagaggcc  attgaaacaa  caaaccaaag  tggaaaatca  cagcgctgcg  tcacaactcc
3721  atggacatac  tttaacttta  atcaatacag  ctgtcacttc  tcaccacagg  attggcagcg
3781  ccttacaaat  gaatataagc  gcttcagacc  taaagcaatg  caagtaaaga  tttacaactt
3841  gcaaataaaa  caaatacttt  caatggtgc  tgacacaaca  tacaacaatg  acctcacagc
3901  tggcgttcac  atctttgtg  atggagagca  tgcttaccca  aatgcatctc  atccatggga
3961  tgaggacgtc  atgcctgatc  ttccatacaa  gacctggaaa  cttttcaat  atggatatat
4021  tcctattgaa  aatgaactcg  cagatcttga  tggaaatgca  gctggaggca  atgctacaga
4081  aaaagcactt  ctgtatcaga  tgccttttt  tctacttgaa  aacagtgacc  accaagtact
4141  tagaactggt  gagagcactg  aatttacttt  taactttgac  tgtgaatggg  ttaacaatga
4201  aagagcatac  attcctcctg  gactaatgtt  taatccaaaa  gtcccaacaa  gaagagttca
4261  gtacataaga  caaaacggaa  gcacagcagc  cagcacaggc  agaattcagc  catactcaaa
4321  accaacaagc  tggatgacag  gacctggcct  gctcagtgca  caaagagtag  gaccacagtc
4381  atcagacact  gctccattca  tggtttgcac  taacccagaa  ggaacacaca  taaacacagg
4441  tgctgcagga  tttggatctg  gctttgatcc  tccaaacgga  tgtctggcac  caactaacct
4501  agaatacaaa  cttcagtggt  accagacacc  agaaggaaca  ggaaataatg  gaaacataat
4561  tgcaaaccca  tcactctcaa  tgcttagaga  ccaactccta  tacaaaggaa  accaaaccac
```

```
4621 atacaatcta gtgggggaca tatggatgtt tccaaatcaa gtctgggaca gatttcctat 4681 caccagagaa atccaatcct ggtgcaaaaa accaagggct gacaaacaca caatcatgga 4741 tccatttgat ggatcaattg caatggatca tcctccaggc actatttta taaaaatggc 4801 aaaaattcca gttccaactg cctcaaatgc agactctatc ctaaacatat actgtactgg 4861 acaagtcagc tgtgaaattg tatgggaggt agaaagatac gcaacaaaga actggcgtcc 4921 agaaagaaga catactgcac tcgggatgtc actgggagga gagagcaact cacgcctac 4981 ataccacgtg gatccaacag gagcatacat ccagcccacg tcatatgatc agtgtatgcc 5041 agtaaaaaca aacatcaata aagtgttgta atcttataag cctctttttt gcttctgctt 5101 acaagttcct cctcaatgga caagcggaaa gtgaagggtg actgtagtcc tgagctcatg 5161 ggttcaagac cacagcccga tggtagtggt gttaccgtct cgaacctagc cgacagccct 5221 tgtacattgt gggggagct gttttgtttg cttatgcaat cgcgaaactc tatatctttt 5281 aatgtgttgt tgttgtaca
```

SEQ ID NO: 3 HBoV NS1 polypeptide encoded by nt 183-2101 of SEQ ID NO: 1 and nt 253-2172 of SEQ ID NO: 2
MAFNPPVIRAFSQPAFTYVFKFPYPQWKEKEWLLHALLAHGTEQSMIQLR
NCAPHPDEDIIRDDLLISLEDRHFGAVLCKAVYMATTTLMSHKQRNMFPR
CDIIVQSELGEKNLHCHIIVGGEGLSKRNAKSSCAQFYGLILAEIIQRCK
SLLATRPFEPEEADIFHTLKKAEREAWGGVTGGNMQILQYRDRRGDLHAQ
TVDPLRFFKNYLLPKNRCISSYSKPDVCTSPDNWFILAEKTYSHTLINGL
PLPEHYRKNYHATLDNEVIPGPQTMAYGGRGPWEHLPEVGDQRLAASSVS
TTYKPNKKEKLMLNLLDKCELNLLVYEDLVANCPELLLMLEGQPGGARL
IEQVLGMHHINVCSNFTALTYLFHLHPVTSLDSDNKALQLLLIQGYNPLA
VGHALCCVLNKQFGKQNTVCFYGPASTGKTNMAKAIVQGIRLYGCVNHLN
KGFVFNDCRQRLVVWWEECLMHQDWVEPAKCILGGTECRIDVKHRDSVLL
TQTPVIISTNHDIYAVVGGNSVSHVHAAPLKERVIQLNFMKQLPQTFGEI
TATEIAALLQWCFNEYDCTLTGFKQKWNLDKIPNSFPLGVLCPTHSQDFT
LHENGYCTDCGGYLPHSADNSMYTDRASETSTGDITPSK SEQ ID NO: 4 HBoV NP-1 polypeptide encoded by nt 2340-2999 of SEQ ID NO: 1 and nt 2410-3069 of SEQ ID NO: 2
MSSGNMKDKHRSYKRKGSPERGERKRHWQTTHHRSRSRSPIRHSGERGSG
SYHQEHPISHLSSCTASKTSDQVMKTRESTSGKKDNRTNPYTVFSQHRAS
NPEAPGWCGFYWHSTRIARDGTNSIFNEMKQQFQQLQIDNKIGWDNTREL
LFNQKKTLDQKYRNMFWHFRNNSDCERCNYWDDVYRRHLANVSSQTEADE
ITDEEMLSAAESMEADASN SEQ ID NO: 5 HBoV ST1 VP1 polypeptide encoded by nt 2986-5001 of SEQ ID NO: 1
MPPIKRQPRGWVLPGYRYLGPFNPLDNGEPVNNADRAAQLHDHAYSELIK
SGKNPYLYFNKADEKFIDDLKDDWSIGGIIGSSFFKIKRAVAPALGNKER
AQKRHFYFANSNKGAKKTKKSEPKPGTSKMSDTDIQDQQPDTVDAPQNAS
GGGTGSIGGGKGSGVGISTGGWVGGSHFSDKYVVTKNTRQFITTIQNGHL
YKTEAIETTNQSGKSQRCVTTPWTYFNFNQYSCHFSPQDWQRLTNEYKRF
RPKAMQVKIYNLQIKQILSNGADTTYNNDLTAGVHIFCDGEHAYPNASHP
WDEDVMPDLPYKTWKLFQYGYIPIENELADLDGNAAGGNATEKALLYQMP
FFLLENSDHQVLRTGESTEFTFNFDCEWVNNERAYIPPGLMFNPKVPTRR
VQYIRQNGSTAASTGRIQPYSKPTSWMTGPGLLSAQRVGPQSSDTAPFMV
CTNPEGTHINTGAAGFGSGFDPPSGCLAPTNLEYKLQWYQTPEGTGNNGN
IIANPSLSMLRDQLLYKGNQTTYNLVGDIWMFPNQVWDRFPITRENPIWC
KKPRADKHTIMDPFDGSIAMDHPPGTIFIKMAKIPVPTATNADSYLNIYC
TGQVSCEIVWEVERYATKNWRPERRHTALGMSLGGESNYTPTYHVDPTGA
YIQPTSYDQCMPVKTNINKVL SEQ ID NO: 6 HBoV ST1 VP2 polypeptide encoded by nt 3373-5001 of SEQ ID NO: 1
MSDTDIQDQQPDTVDAPQNASGGGTGSIGGGKGSGVGISTGGWVGGSHFS
DKYVVTKNTRQFITTIQNGHLYKTEAIETTNQSGKSQRCVTTPWTYFNFN
QYSCHFSPQDWQRLTNEYKRFRPKAMQVKIYNLQIKQILSNGADTTYNND
LTAGVHIFCDGEHAYPNASHPWDEDVMPDLPYKTWKLFQYGYIPIENELA
DLDGNAAGGNATEKALLYQMPFFLLENSDHQVLRTGESTEFTFNFDCEWV
NNERAYIPPGLMFNPKVPTRRVQYIRQNGSTAASTGRIQPYSKPTSWMTG
PGLLSAQRVGPQSSDTAPFMVCTNPEGTHINTGAAGFGSGFDPPSGCLAP
TNLEYKLQWYQTPEGTGNNGNIIANPSLSMLRDQLLYKGNQTTYNLVGDI
WMFPNQVWDRFPITRENPIWCKKPRADKHTIMDPFDGSIAMDHPPGTIFI
KMAKIPVPTATNADSYLNIYCTGQVSCEIVWEVERYATKNWRPERRHTAL
GMSLGGESNYTPTYHVDPTGAYIQPTSYDQCMPVKTNINKVL SEQ ID NO: 7 HBoV ST2 VP1 polypeptide encoded by nt 3056-5071 of SEQ ID NO: 2
MPPIKRQPRGWVLPGYRYLGPFNPLDNGEPVNNADRAAQLHDHAYSELIK -continued
SGKNPYLYFNKADEKFIDDLKDDWSIGGIIGSSFFKIKRAVAPALGNKER

AQKRHFYFANSNKGAKKTKKSEPKPGTSKMSDTDIQDQQPDTVDAPQNTS

GGGTGSIGGGKGSGVGISTGGWVGGSHFSDKYVVTKNTRQFITTIQNGHL

YKTEAIETTNQSGKSQRCVTTPWTYFNFNQYSCHFSPQDWQRLTNEYKRF

RPKAMQVKIYNLQIKQILSNGADTTYNNDLTAGVHIFCDGEHAYPNASHP

WDEDVMPDLPYKTWKLFQYGYIPIENELADLDGNAAGGNATEKALLYQMP

FFLLENSDHQVLRTGESTEFTFNFDCEWVNNERAYIPPGLMFNPKVPTRR

VQYIRQNGSTAASTGRIQPYSKPTSWMTGPGLLSAQRVGPQSSDTAPFMV

CTNPEGTHINTGAAGFGSGFDPPNGCLAPTNLEYKLQWYQTPEGTGNNGN

IIANPSLSMLRDQLLYKGNQTTYNLVGDIWMFPNQVWDRFPITRENPIWC

KKPRADKHTIMDPFDGSIAMDHPPGTIFIKMAKIPVPTASNADSYLNIYC

TGQVSCEIVWEVERYATKNWRPERRHTALGMSLGGESNYTPTYHVDPTGA

YIQPTSYDQCMPVKTNINKVL

SEQ ID NO: 8 HBoV ST2 VP2 polypeptide encoded by
nt 3343-5071 of SEQ ID NO: 2
MSDTDIQDQQPDTVDAPQNTSGGGTGSIGGGKGSGVGISTGGWVGGSHFS

DKYVVTKNTRQFITTIQNGHLYKTEAIETTNQSGKSQRCVTTPWTYFNFN

QYSCHFSPQDWQRLTNEYKRFRPKAMQVKIYNLQIKQILSNGADTTYNND

LTAGVHIFCDGEHAYPNASHPWDEDVMPDLPYKTWKLFQYGYIPIENELA

DLDGNAAGGNATEKALLYQMPFFLLENSDHQVLRTGESTEFTFNFDCEWV

NNERAYIPPGLMFNPKVPTRRVQYIRQNGSTAASTGRIQPYSKPTSWMTG

PGLLSAQRVGPQSSDTAPFMVCTNPEGTHINTGAAGFGSGFDPPNGCLAP

TNLEYKLQWYQTPEGTGNNGNIIANPSLSMLRDQLLYKGNQTTYNLVGDI

-continued
WMFPNQVWDRFPITRENPIWCKKPRADKHTIMDPFDGSIAMDHPPGTIFI

KMAKIPVPTASNADSYLNIYCTGQVSCEIVWEVERYATKNWRPERRHTAL

GMSLGGESNYTPTYHVDPTGAYIQPTSYDQCMPVKTNINKVL

SEQ ID NO: 9 Primer 188F
GAGCTCTGTAAGTACTATTAC

SEQ ID NO: 10 Primer 542R
CTCTGTGTTGACTGAATACAG

REFERENCES

1 Young N S, Brown K E. Parvovirus B19. N Engl J Med 2004; 350(6):586-97.
2 Jones M S, et al., J Virol 2005; 79(13):8230-6.
3 Allander T. et al., *PNAS USA* 2001; 98:11609-14
4 Allander T. et al., *PNAS USA* 2005; 102(36):12891-12896.
Schwartz, D., et al., (2002) *Virology* 302, 219-23.
6 Chen, K. C., et al., (1986) *J Virol* 60, 1085-97
7 Deiman B, van Aarle P & Sillekens P, *Molecular Biotechnology* 2002, 20:163-178.
8 U.S. Pat. No. 4,683,195
9 Mullis et al. Cold Spring Harbor Symp. Quant. Biol., 51:263,
10 Ehrlich (ed), PCR technology, Stockton Press, NY, 1989
11 Ehrlich et al. Science, 252:1643-1650, 1991
12 "PCR protocols; A Guide to Methods and Applications", Eds. Innis et al. Academic Press, New York, 1990.
13 Kontermann, R & Dubel, S, *Antibody Engineering*, Springer-Verlag New York, LLC; 2001, ISBN: 3540413545.
14 WO92/01047
Mendez, M. et al. (1997) Nature Genet, 15(2): 146-156
16 Nygren et al. (1997) Current Opinion in Structural Biology, 7: 463-469.
17 WO/0034784

---

The invention claimed is:

1. A method of testing a sample for the presence of a human bocavirus, comprising testing the sample for the presence or absence of at least one molecule selected from the group consisting of:
   a) a nucleic acid sequence comprising a nucleotide sequence of a ST2 isolate of human bocavirus of SEQ ID NO: 2;
   b) a bocaviral nucleic acid molecule that encodes a VP1 polypeptide of human bocavirus ST2 of SEQ ID NO: 7;
   c) a nucleic acid molecule comprising a nucleotide sequence that encodes a polypeptide having at least 95% sequence identity with the human bocavirus ST2 polypeptide VP1 of SEQ ID NO: 7; and
   d) a nucleic acid molecule comprising a nucleotide sequence that has at least 95% sequence identity with the ST2 isolate of SEQ ID NO: 2.

2. A method of testing a sample for the presence or absence of antibodies to human bocavirus, comprising determining whether antibodies in the sample bind to at least one polypeptide encoded by a nucleic acid selected from the group consisting of
   a) a nucleic acid sequence comprising a nucleotide sequence of a ST2 isolate of human bocavirus of SEQ ID NO: 2;
   b) a bocaviral nucleic acid molecule that encodes a VP1 polypeptide of human bocavirus ST2 of SEQ ID NO: 7;
   c) a nucleic acid molecule comprising a nucleotide sequence that encodes a polypeptide having at least 95% sequence identity with the human bocavirus ST2 polypeptide VP1 of SEQ ID NO: 7; and
   d) a nucleic acid molecule comprising a nucleotide sequence that has at least 95% sequence identity with the ST2 isolate of SEQ ID NO: 2.

3. A method according to claim 2, comprising performing an enzyme immunoassay to detect binding of antibodies in the sample to the polypeptide.

4. A kit for testing a sample for the presence of absence of antibodies to human bocavirus, comprising a polypeptide attached to a support wherein the polypeptide is encoded by a nucleic acid selected from the group consisting of
   a) a nucleic acid sequence comprising a nucleotide sequence of a ST2 isolate of human bocavirus of SEQ ID NO: 2;
   b) a bocaviral nucleic acid molecule that encodes a VP1 polypeptide of human bocavirus ST2 of SEQ ID NO: 7;
   c) a nucleic acid molecule comprising a nucleotide sequence that encodes a polypeptide having at least 95% sequence identity with the human bocavirus ST2 polypeptide VP1 of SEQ ID NO: 7; and
   d) a nucleic acid molecule comprising a nucleotide sequence that has at least 95% sequence identity with the ST2 isolate of SEQ ID NO: 2, wherein said kit further comprises an anti-immunoglobulin antibody molecule linked to an enzyme that catalyzes conversion of a substrate to a detectable product, and a substrate for the enzyme.

5. A method of testing a sample for the presence or absence of a human bocavirus, comprising testing the sample for the presence of at least one nucleic acid molecule consisting of an isolated fragment of sequence SEQ ID NO: 2, wherein the fragment is selected from the group consisting of:
   a) nucleotides 253 to 2172 of SEQ ID NO:2;
   b) nucleotides 2410 to 3069 of SEQ ID NO:2;
   c) nucleotides 3056 to 5071 of SEQ ID NO:2;
   d) nucleotides 3443 to 5071 of SEQ ID NO:2;
   e) a nucleotide sequence with at least 95% sequence identity with the isolated fragment of a), b), c) or d).

6. A method of testing a sample for the presence or absence of a human bocavirus, wherein the method comprises testing the sample for the presence of at least one isolated polypeptide encoded by a bocavirus nucleic acid, wherein the polypeptide is selected from the group consisting of:
   a) a human bocavirus ST2 polypeptide VP1 of SEQ ID NO: 7;
   b) a human bocavirus ST2 polypeptide VP2 of SEQ ID NO: 8;
   c) a human bocavirus ST2 polypeptide NP1 of SEQ ID NO: 4;
   d) a human bocavirus ST2 polypeptide NS1 of SEQ ID NO: 3; and
   e) a human bocavirus ST2 polypeptide having at least 95% sequence identity with the human bocavirus ST2 polypeptides of a), b), c) or d).

* * * * *